US006733762B1

(12) United States Patent
Fasano et al.

(10) Patent No.: US 6,733,762 B1
(45) Date of Patent: May 11, 2004

(54) METHOD OF USING ZOT TO INHIBIT LYMPHOCYTE PROLIFERATION IN AN ANTIGEN-SPECIFIC MANNER

(75) Inventors: Alessio Fasano, West Friendship, MD (US); Marcelo B. Sztein, Columbia, MD (US); Ruiliang Lu, Baltimore, MD (US); Michael K. Tanner, Crestwood, KY (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 09/786,319

(22) PCT Filed: Sep. 9, 1999

(86) PCT No.: PCT/US99/18842

§ 371 (c)(1),
(2), (4) Date: May 3, 2001

(87) PCT Pub. No.: WO00/15252

PCT Pub. Date: Mar. 23, 2000

Related U.S. Application Data

(60) Provisional application No. 60/100,266, filed on Sep. 14, 1998.

(51) Int. Cl.$^7$ ............................................. A61K 39/106
(52) U.S. Cl. ................................................... 424/261.1
(58) Field of Search .......................... 424/261.1, 184.1

(56) References Cited

U.S. PATENT DOCUMENTS 5,945,510 A    8/1999   Fasano

OTHER PUBLICATIONS

Goldsby & Kuby et al. Immunology WH Freeman pp. 281, 384, 485, 2002.*
Germain, *Fundamental Immunology*, 3$^{rd}$ Ed., Edited by William E. Paul, Raven Press, Ltd., New York, pp. 629–676 (1993).
Revel et al, "Cell Junctions in Development, with Particular Reference to the Neural Tube", pp. 443–455.
Lin et al, *Pharmaceutical Research*, 8(7):919–924 (1991).
Citi et al, *Nature*, 333:272–276 (1988).
Guan et al, *Letters to Nature*, 358:690–692 (1992).
Hartwig et al, *Letters to Nature*, 356:618–622 (1992).
Thelan et al, *Letters to Nature*, 351:320–322 (1991).
Thoma et al, *Pharmazie*, 46:331–336 (1991).
Gumbiner et al, *Proc. Natl. Acad. Sci., USA*, 88:3460–3464 (1991).
Madara et al, *J. Membrane Biol.*, 100:149–164 (1987).
Fromm et al, *J. Membrane Biol.*, 87:141–150 (1985).
Madara, *Textbook of Secretory Diarrhea*, Chapter 11, pp. 125–138, edited by E. Lebenthal and M. Duffey, Raven Press, Ltd., New York (1990).
King, "Tablets, Capsules, and Pills", Chapter 89, pp. 1553–1584.

Sztein et al, *New Generation Vaccines*, 2$^{nd}$ Ed., Revised and Expanded, Chapter 10, pp. 99–125 (1997).
Sztein et al, *Journal of Immunology*, pp. 3987–3993 (1995).
Townsend et al, *Cell*, 44:959–968 (1986).
Sprent, *Cell*, 76:315–322 (1994).
Peters et al, *Immunology Today*, 17(6):273–278 (1996).
Shearer et al, *Immunology Today*, 17(1):21–24 (1996).
Sedegah et al, *Journal of Immunology*, 149(3):966–971 (1992).
Reed et al, *Journal of Immunology*, 137(1):150–154 (1986).
Fearon et al, *Science*, 272:50–54 (1996).
Malik et al, *Proc. Natl. Acad. Sci.. USA*, 88:3300–3304 (1991).
Banchereau et al, *Advances in Immunology*, 52:125–262 (1992).
Yoshitomi et al, *Chem. Pharm. Bull.*, 40(7):1902–1905 (1992).
Rosen et al, *J. Exp. Med.*, 172:1211–1215 (1990).
Stevenson et al, *Molecular and Cellular Biochemistry*, 83:129–145 (1988).
Digenis et al, *J. of Pharmaceutical Sciences*, 83(7):915–921 (1994).
Davis, "Disc Electrophoresis–II: Method and Application to Human Serum Proteins", Part II, Clinical Applications, pp. 404–427.
Johnson et al, *J. of Clin. Microbiology*, 31(3):732–733 (1993).
Schneeberger et al, *J. Cell Sci.*, 32:307–324 (1978).
Levine et al, *Infection and Immunity*, 56(1):161–167 (1988).
Gilula et al, *Developmental Biology*, 50:142–168 (1976).
Magnuson et al, *Developmental Biology*, 67:214–224 (1978).
Zahraoui et al, *J. of Cell Biol.*, 124(1&2):101–115 (1994).
Tsukita et al, *J. of Cell Biol.*, 123(5):1049–1053 (1993).
Drenckhahn et al, *J. of Cell Biol.*, 107:1037–1048 (1988).
Sardet et al, *J. of Cell Biol.*, 80:96–117 (1979).
Mazariegos et al, *J. of Cell Biol.*, 98:1865–1877 (1984).
Zhong et al, *J. of Cell Biol.*, 120(2):477–483 (1993).
Milks et al, *J. of Cell Biol.*, 103(No. 6, Pt. 2):2729–2738 (1986).
Ridley et al, *Cell*, 70:401–410 (1992).
Shasby et al, *Amer. Physiol. Soc.*, pp. C781–C788 (1988).

(List continued on next page.)

*Primary Examiner*—Patrick J. Nolan
(74) *Attorney, Agent, or Firm*—Sughrue Mion, PLLC

(57) ABSTRACT

Methods of using Zot or zonulin as an antigen specific inhibitor of APC activity and lymphocyte proliferation, being primarily useful in the field of immunoregulation and immunotherapy as described. Specifically, Zot and zonulin inhibit antigen presenting cell-mediated antigen-specific lymphocyte proliferation in a dose dependent manner. This effect is associated with the presence of a macrophage surface receptor to which Zot binds in a specific and saturable way. This down-regulation of the immune response is, at least in part, associated with a decreased uptake of antigen.

2 Claims, 13 Drawing Sheets

OTHER PUBLICATIONS

Ridley et al, *Cell,* 70:389–399 (1992).
Linsley et al, *Annu. Rev. Immunol.* 11:191–212 (1993).
Clark et al, *Annu. Rev. Immunol.,* 9:97–127 (1991).
Kaufman et al, *Annu. Rev. Immunol.,* 11:129–163 (1993).
Lenschow et al, *Annu. Rev. Immunol.,* 14:233–258 (1996).
Baudry et al, *Infection and Immunity,* 60(2):428–434 (1992).
Fasano et al, *Proc. Natl. Acad. Sci., USA,* 88:5242–5246 (1991).
Diamond, The Epithelial Junction: Bridge, Gate, and Fence, 21$^{st}$ Bowditch Lecture, pp. 10–18, Los Angeles, CA.
Nash et al, *Laboratory Investigation,* 59(4):531–537 (1988).
Madara, *J. Clin. Invest.,* 83:1089–1094 (1989).

Ettehadi et al, *Clinical and Experimental Immunology,* 93(1):146–151 (1994).

Maini et al, "TNF Blockade in Rheumatoid Arthritis: Implications for Therapy and Pathogenesis. Review Article", 105:257–263 (1997).

Maurano et al, *Gastroenterology,* 116(4, Part 2):A834, Abstract (1999).

Marinaro et al, *Infection and Immunity,* 67(3):1287–1291 (1999).

* cited by examiner

SEQUENCE LISTING

<160> NUMBER OF SEQ ID NOS: 8

<210> SEQ ID NO 1
<211> LENGTH: 18
<212> TYPE: PRT
<213> ORGANISM: Human

<400> SEQUENCE: 1

Asn Asp Gln Pro Pro Pro Ala Gly Val Thr Ala Tyr Asp Tyr Leu Val
 1               5                  10                  15

Ile Gln

<210> SEQ ID NO 2
<211> LENGTH: 20
<212> TYPE: PRT
<213> ORGANISM: Human
<220> FEATURE:
<221> NAME/KEY: UNSURE
<222> LOCATION: (10)
<223> OTHER INFORMATION: X at position 10 is an amino acid.

<400> SEQUENCE: 2

Glu Val Gln Leu Val Glu Ser Gly Gly Xaa Leu Val Gln Pro Gly Gly
 1               5                  10                  15

Ser Leu Arg Leu
            20

<210> SEQ ID NO 3
<211> LENGTH: 23
<212> TYPE: DNA
<213> ORGANISM: synthetic construct

<400> SEQUENCE: 3
cgggatcccg tatgagtatc ttt                                              23

<210> SEQ ID NO 4
<211> LENGTH: 24
<212> TYPE: DNA
<213> ORGANISM: synthetic construct

<400> SEQUENCE: 4
cccaagcttg ggtcaaaata tact                                             24

<210> SEQ ID NO 5
<211> LENGTH: 18
<212> TYPE: DNA
<213> ORGANISM: synthetic construct

<400> SEQUENCE: 5
tcatcacggc gcgccagg                                                    18

<210> SEQ ID NO 6
<211> LENGTH: 22
<212> TYPE: DNA
<213> ORGANISM: synthetic construct

<400> SEQUENCE: 6
ggaggtctag aatctgcccg at                                               22

<210> SEQ ID NO 7
<211> LENGTH: 8
<212> TYPE: PRT

-continued

```
<213> ORGANISM: synthetic construct

<400> SEQUENCE: 7

Gly Gly Val Leu Val Gln Pro Gly
  1               5

<210> SEQ ID NO 8
<211> LENGTH: 8
<212> TYPE: PRT
<213> ORGANISM: synthetic construct

<400> SEQUENCE: 8

Val Gly Val Leu Gly Arg Pro Gly
  1               5
```

METHOD OF USING ZOT TO INHIBIT LYMPHOCYTE PROLIFERATION IN AN ANTIGEN-SPECIFIC MANNER

CROSS-REFERENCE TO RELATED APPLICATIONS

This application is a 371 of PCT/US99/18842 filed Sep. 9, 1999 (now WO 00/15252); which is basted on U.S. Provisional Application No. 60/100,266, filed Sep. 14, 1998.

This application is an application filed under 35 U.S.C. § 111(a) claiming benefit pursuant to 35 U.S.C. § 119(e)(i) of the filing date of the Provisional Application No. 60/100, 266, filed Sep. 14, 1998, pursuant to 35 U.S.C. § 111(b).

The development of the present invention was supported by the University of Maryland, Baltimore. Certain studies described herein were supported by the National Institutes of Health, NIH Grant No. DK-48373. The Government may have certain rights.

FIELD OF THE INVENTION

The present invention relates to antigen-specific down-regulation of an immune response using Zot or zonulin. Specifically, the present invention provides a method for inhibiting antigen presenting cell-mediated antigen-specific lymphocyte proliferation in a dose-dependent manner by administering an effective amount of Zot or zonulin.

BACKGROUND OF THE INVENTION

I. Tight Junctions and the Actin Cytoskeleton

The tight junctions (hereinafter "tj") or zonula occludens (hereinafter "ZO") are one of the hallmarks of absorptive and secretory epithelia (Madara, *J. Clin. Invest.*, 83:1089–1094 (1989); and Madara, *Textbook of Secretory Diarrhea* Eds. Lebenthal et al, Chapter 11, pages 125–138 (1990). As a barrier between apical and basolateral compartments, they selectively regulate the passive diffusion of ions and water-soluble solutes through the paracellular pathway (Gumbiner, *Am. J. Physiol.*, 253(Cell Physiol. 22):C749–C758 (1987)). This barrier maintains any gradient generated by the activity of pathways associated with the transcellular route (Diamond, *Physiologist*, 20:10–18 (1977)).

There is abundant evidence that ZO, once regarded as static structures, are in fact dynamic and readily adapt to a variety of developmental (Magnuson et al, *Dev. Biol.*, 67:214–224 (1978); Revel et al, *Cold Spring Harbor Symp. Quant. Biol.*, 40:443–455 (1976); and Schneeberger et al, *J. Cell Sci.*, 32:307–324 (1978)), physiological (Gilula et al, *Dev. Biol.*, 50:142–168 (1976); Madara et al, *J. Membr. Biol.*, 100:149–164 (1987); Mazariegos et al, *J. Cell Biol.*, 98:1865–1877 (1984); and Sardet et al, *J. Cell Biol.*, 80:96–117 (1979)), and pathological (Milks et al, *J. Cell Biol.*, 103:2729–2738 (1986); Nash et al, *Lab. Invest.*, 59:531–537 (1988); and Shasby et al, *Am. J. Physiol.*, 255(*Cell Physiol.*, 24):C781–C788 (1988)) circumstances. The regulatory mechanisms that underlie this adaptation are still not completely understood. However, it is clear that, in the presence of $Ca^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist*, 20:10–18 (1977)). A candidate for the transmembrane protein strands, occluding, has been identified (Furuse et al, *J. Membr. Biol.*, 87:141–150 (1985)).

Six proteins have been identified in a cytoplasmic submembranous plaque underlying membrane contacts, but their function remains to be established (Diamond, supra). ZO-1 and ZO-2 exist as a heterodimer (Gumbiner et al, *Proc. Natl. Acad. Sci., USA*, 88:3460–3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.*, 83:129–145 (1988)). Two other proteins, cingulin (Citi et al, *Nature* (London), 333:272–275 (1988)) and the 7H6 antigen (zhong et al, *J. Cell Biol.*, 120:477–483 (1993)) are localized further from the membrane and have not yet been cloned. Rab 13, a small GTP binding protein has also recently been localized to the junction region (Zahraoui et al, *J. Cell Biol.*, 124:101–115 (1994)). Other small GTP-binding proteins are known to regulate the cortical cytoskeleton, i.e., rho regulates actin-membrane attachment in focal contacts (Ridley et al, *Cell*, 70:389–399 (1992)), and rac regulates growth factor-induced membrane ruffling (Ridley et al, *Cell*, 70:401–410 (1992)). Based on the analogy with the known functions of plaque proteins in the better characterized cell junctions, focal contacts (Guan et al, *Nature*, 3:690–692 (1992)), and adherens junctions (Tsukita et al, *J. Cell Biol.*, 1:1049–1053 (1993)), it has been hypothesized that tj-associated plaque proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.*, 107:1037–1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS"). MARCKS is a specific protein kinase C (hereinafter "PKC") substrate that is associated with the cytoplasmic face of the plasma membrane (Aderem, *Elsevier Sci. Pub.* (*UK*), pages 438–443 (1992)). In its non-phosphorylated form, MARCKS crosslinks to the membrane actin. Thus, it is likely that the actin meshwork associated with the membrane via MARCKS is relatively rigid (Hartwig et al, *Nature*, 356:618–622 (1992)). Activated PKC phosphorylates MARCKS, which is released from the membrane (Rosen et al, *J. Exp. Med.*, 172:1211–1215 (1990); and Thelen et al, *Nature*, 351:320–322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra). These data suggest that the F-actin network may be rearranged by a PKC-dependent phosphorylation process that involves actin-binding proteins (MARCKS being one of them).

II. Zonula Occludens Toxin ("Zot") and Zonulin

Most *Vibrio cholerae* vaccine candidates constructed by deleting the ctxa gene encoding cholera toxin (CT) are able to elicit high antibody responses, but more than one-half of the vaccinee still develop mild diarrhea (Levine et al, *Infect. Immun.*, 56(1):161–167 (1988)). Given the magnitude of the diarrhea induced in the absence of CT, it was hypothesized that *V. cholerae* produce other enterotoxigenic factors, which are still present in strains deleted of the ctxa sequence (Levine et al, supra). As a result, a second toxin, zonula occludens toxin (hereinafter "Zot) elaborated by *V. cholerae*, and which contribute to the residual diarrhea, was discovered (Fasano et al, *Proc. Nat. Acad. Sci., USA*, 8:5242–5246 (1991)). The zot gene is located immediately adjacent to the ctx genes. The high percent concurrence of the zot gene with the ctx genes among *V. cholerae* strains (Johnson et al, *J. Clin. Microb.*, 31/3:732–733 (1993); and Karasawa et al, *FEBS Microbiology Letters*, 106:143–146 (1993)) suggests a possible synergistic role of Zot in the causation of acute dehydrating diarrhea typical of cholera. Recently, the zot gene has also been identified in other enteric pathogens (Tschape, 2nd *Asian-Pacific Symposium on Typhoid fever and other Salmonellosis*, 47(Abstr.) (1994)).

It has been previously found that, when tested on rabbit ileal mucosa, Zot increases the intestinal permeability by modulating the structure of intercellular tight junctions (Fasano et al, supra). It has been found that as a consequence of modification of the pericellular pathway, the intestinal mucosa becomes more permeable. It also was found that Zot does not affect $Na^+$-glucose coupled active transport, is not cytotoxic, and fails to completely abolish the transepithelial resistance (Fasano et al, supra).

More recently, it has been found that Zot is capable of reversibly opening tight junctions in the intestinal mucosa, and thus Zot, when co-administered with a therapeutic agent, is able to effect intestinal delivery of the therapeutic agent, when employed in an oral dosage composition for intestinal drug delivery (WO 96/37196, U.S. Pat. No. 5,827,534 and U.S. Pat. No. 5,665,389; each of which is incorporated by reference herein in their entirety). It has also been found that Zot is capable of reversibly opening tight junctions in the nasal mucosa, and thus Zot, when co-administered with a therapeutic agent, is able to enhance nasal absorption of a therapeutic agent (WO 98/30211 and U.S. Pat. No. 5,908,825; which is incorporated by reference herein in its entirety).

In U.S. Pat. No. 5,864,014 and U.S. Pat. No. 5,912,323; which are incorporated by reference herein in their entirety, Zot receptors from CaCo2 cells, heart, intestinal and brain tissue has been identified and isolated. The Zot receptors represent the first step of the pericellular pathway involved in the regulation of epithelial intestinal and nasal permeability.

In U.S. Pat. No. 5,945,510, which is incorporated by reference herein in its entirety, mammalian proteins that are immunologically and functionally related to Zot, and that function as the physiological modulator of mammalian tight junctions, have been identified and purified. These mammalian proteins, referred to as "zonulin", are useful for enhancing absorption of therapeutic agents across tight junctions of intestinal and nasal mucosa, as well as across tight junctions of the blood brain barrier. These proteins are further characterized by the ability to bind to the Zot receptors.

In pending U.S. patent application Ser. No. 09/127,815 filed Aug. 3, 1998, entitled "Peptide Antagonists of Zonulin and Methods for Use of the Same", which is incorporated by reference herein in its entirety, peptide antagonists of zonulin have been identified. Said peptide antagonists bind to Zot receptor, yet do not function to physiologically modulate the opening of mammalian tight junctions. The peptide antagonists competitively inhibit the binding of Zot and zonulin to the Zot receptor, thereby inhibiting the ability of Zot and zonulin to physiologically modulate the opening of mammalian tight junctions.

III. Antiaen Presenting Cells and Immune Responses

For a complete discussion of immune responses and immunomodulation, see Chapter 10 "Recent Advances in Immunology", by Sztein et al, *New Generation of Vaccines*, pages 99–125, Eds. Levine et al (1997), the disclosure of which is hereby incorporated by reference.

One of the primary mechanisms of protection against infectious agents involves specific or acquired immunity. In contrast to innate immunity, the effector mechanisms of acquired immunity that include, among others, antibodies, cytotoxic lymphocytes (hereinafter "CTL"), T lymphocyte-derived cytokines (such as IFN-γ, IL-4, etc.) are induced following exposure to antigens or infectious agents and increase in magnitude with successive exposures to the specific antigens. This ability to "recall" previous exposures to antigens and respond rapidly with immunological effector responses of increased magnitude (immunologic memory) constitutes the foundation for immunoprophylactic vaccination against infectious agents. The chief cell types involved in specific immune responses are T and B lymphocytes.

B lymphocytes or B cells are derived from the bone marrow and are the precursors of antibody secreting cells (plasma cells). B cells recognize antigens (proteins, carbohydrates or simple chemical groups) through immunoglobulin receptors on the cell membrane (Fearon et al, *Science*, 272:50–53 (1996); ziegler-Heitbroack et al, *Immunol. Today*, 14:121–152 (1993); and Banchereau et al, *Adv. Immunol.*, 52;125–262 (1992)). After triggering by antigen, they clonally expand and switch their expression of antibody isotype (e.g., IgM to IgG, IgE or IgA) under the influence of cytokines derived from T cells, macrophages and other cell types. Somatically-mutated, high affinity B cells are generated and selected by antigen in and around the germinal centers that are formed in lymph nodes, spleen, Peyers' patches and more disorganized lymphatic aggregates of the peripheral lymphoid system (Banchereau et al, (1996) supra; Clark et al, *Ann. Rev. Immunol.*, 9:97–127 (1991); and MacLennan et al, *Immunol. Today*, 14:29–34 (1993)). They are the basis for B cell memory.

T lymphocytes or T cells, in contrast to B cells, recognize peptides derived from protein antigens that are presented on the surface of antigen presenting cells (hereinafter "APC") in conjunction with Class I or Class II major histocompatibility complex (MHC) molecules. Clones of T lymphocytes expressing T cell receptors (hereinafter "TCR") of appropriate affinity are triggered by antigen to proliferate and develop into effector cells (Fearon, (1996) supra; Sprent et al *Cell*, 76:315–322 (1994); and Hendrick et al, Germain, *Fundamental Immunology*, 3rd ed., pages 629–676 (1993)). After elimination of the infectious agent, the antigen-specific clones remain as memory T cells that, upon subsequent exposures to antigen, provide a stronger, more rapid and sometimes qualitatively different specific immune response.

There are two main populations of T cells, those expressing CD4 molecules and those expressing CD8 molecules. CD4 and CD8 molecules are T cell surface. glycoproteins that serve as important accessory molecules (co-receptors) during antigen presentation by binding to Class II and Class I MHC molecules, respectively (Hendrick et al, supra (1993)). Thus, CD4 and CD8 molecules play a significant role in stabilizing the interactions of T cells and APC initiated by the specific binding of the TCR complex to antigenic peptides presented in association with MHC molecules. Consequently, CD4 and CD8 molecules, originally used primarily as markers to identify T cell populations with different functional characteristics, play a major role in Class II MHC-restricted and Class I MHC-restricted T cell activation. CD4+ cells (T helper or Th) are mainly involved in inflammatory responses and providing help for antibody production by B cells, while CD8+ cells (T cytotoxic or Tc) compose the majority of ° CTL primarily involved in Class I MHC-restricted killing of target cells infected by pathogenic organisms, including bacteria, viruses and parasites (Sztein et al, *J. Immunol.*, 155:3987–3993 (1995); Kaufman, *Ann. Rev. Immunol.*, 11:129–163 (1993) and *Immunol. Today*, 9:168–174 (1988); Townsend et al, *Cell*, 44:959–968 (1986); Malik et al, *Proc. Natl. Acad. Sci., USA*, 88:3300–3304 (1991); Sedegah et al, *J. Immunol.*, 1:966–971 (1992); and Shearer et al, *Immunol. Today*, 17:21–24 (1996)).

Successful antigen specific activation of T cells resulting in T cell expansion and differentiation (or lymphocyte proliferation) requires a first signal provided by the interaction of TCR on the surface of T cells with MHC-antigen complexes on APC and a second, complementary, signal provided by soluble factors, such as IL-2, or binding of CD28 (a co-stimulatory molecule) to members of the B7 family (e.g., CD80 (B7-1) or CD86 (B7-2)) on APC (Lenschow, *Ann. Rev. Immunol.*, 14:233–258(1996); and Linsley et al, *Ann. Rev. Immunol.*, 11:191–212(1993)). The study of the CD28/B7 co-stimulatory pathway and other adhesion molecules that help stabilize T cell-APC interactions (and which also appear to play critical in roles in lymphocyte homing), is one of the key areas in which many significant advances have been made in recent years.

Presentation of antigens to T cells involves a series of intracellular events within the APC, including the generation of antigenic peptide fragments, binding of these peptides to MHC molecules to form stable peptide-MHC complexes and transport of these complexes to the cell surface where they can be recognized by TCR in the surface of T cells. Evidence has accumulated for the existence of two main pathways of antigen processing and presentation ("classical pathways"). One of these pathways, the "cytosolic pathway", is predominantly used for presentation of peptides produced endogenously in the APC, such as viral proteins, tumor antigens and self-peptides, associated with Class I MHC molecules (Hendrick et al, supra; and Germain, supra (1993)). The presentation of large numbers of self-peptides complexed to Class I MHC molecules results from the inability of APC to differentiate between self and non-self. Under normal conditions, most T cells selected to recognize self-peptides are eliminated during T cell differentiation or are actively down regulated, and consequently can not be activated by self-peptide-Class I MHC complexes. The second "classical pathway" of antigen processing and presentation, "endosomal pathway", which is predominantly used for presentation of soluble exogenous antigens bound to Class II MHC molecules, involves the capture of antigen by APC, either by binding to a specific receptor or by uptake in the fluid phase by macropinocytosis (Lanzavecchia, *Curr. Opin. Immunol.*, 8:348–354 (1996)). Triggering of T cells through the TCR has been shown with as few as 200–600 peptide/MHC complexes in the case of influenza nucleoproteins (Falk et al, *Semin. Immunol.*, 5:81–94 (1993)). In most immune responses, antigenic epitopes associated with Class I MHC molecules trigger the activation of CD8+ CTL responses, while antigenic fragments (epitopes) derived from soluble proteins complexed to Class II MHC molecules are recognized by CD4+ Th cells. These findings are among the most important contributions made over the past few years on the mechanisms involved in the early stages of immune activation and are critical for the development of successful vaccines.

As mentioned above, there are two "classical" pathways of antigen processing and presentation. The Class I MHC pathway is that most commonly used for processing of cellular proteins present in most, if not all, cellular compartments, including the cytosol, nucleus and mitochondria (Falk et al, supra (1993)) for recognition by CD8+ CTL. The Class II MHC pathway is predominantly used for processing and presentation of exogenous antigens, such as proteins produced by extracellular bacteria and other infectious microorganisms that can be presented to CD4+ Th cells. Both Class I and II MHC molecules bind peptide antigens through the use of surface If "receptors" or "binding clefts". However, the route of antigen processing and preparation varies dramatically between the two. Class I antigens are processed and prepared by the "cytosolic pathway". Specifically, peptides synthesized intracellularly are degraded into small protein fragments which are then carried across the membrane of the endoplasmic reticulum (ER). Inside the ER, antigenic fragments bind to Class I MHC molecules forming a complex that is then transported to the Golgi apparatus and ultimately to the cell surface where they are recognized by TCR, signalling antigen-specific CTL expansion and differentiation, the first step of an immune response. Class II antigens, on the other hand, are processed and prepared by the "endosomal pathway". Specifically, native antigens are captured by a circulating APC, the antigen binding to a specific or nonspecific receptor. The antigen is then internalized by the APC by a mechanism of receptor-mediated endocytosis or pinocytosis. The internalized antigen is then localized in an endosome, a membrane bound vesicle involved in the intracellular transport and degradation of the antigen. Cleaved peptide fragments then bind to Class II MHC molecules to form a complex that is transported through the Golgi apparatus, into the endosomal compartment, and to the cell surface to become recognized by TCR, again signaling the antigen-specific Th cell expansion and differentiation.

APC play a vital role in the generation of an immune response. For presentation of processed antigens to CTL in a Class I-restricted fashion, the APC must express Class I MHC molecules and have the ability to express on the cell surface endogenously produced proteins complexed to Class I MHC molecules. Almost all cells endogenously producing viral, parasitic, or bacterial proteins or tumor antigens that gain access to the cytosol can function as APC. For presentation of processed antigens to Th cells in a Class II restricted fashion, the APC must be able to recognize and bind the antigen through specific or nonspecific receptors for the particular antigen. Cells that most efficiently present antigens to Th lymphocytes, so called professional APC include dendritic cells (DC), macrophages, B lymphocytes, Langerhans cells, and, in certain instances, human endothelial cells (Lanzavecchia, supra (1996)).

DC that originate in the bone marrow are considered to be the most efficient APC for presentation of soluble antigens. DC capture antigens on the periphery and migrate to the spleen or lymph nodes, where they efficiently activate the Th cells, particularly naive T cells (Lanzavecchia, supra (1996);

and Peters et al, *Immunol. Today*, 17:273–278 (1996)). Several unique characteristics enable DC to function so effectively as antigen presenters. Specifically, they have the ability to internalize soluble antigens by several mechanisms, including constitutive macropinocytosis, internalization of antigen-antibody complexes through CD32 receptor binding, and internalization of mannosylated or fucosylated antigens through mannose receptor binding. This allows DC to sample large amounts of fluid in short periods of time, accumulating them in a lysosomal compartment containing Class II MHC molecules and proteases. DC also constitutively express a number of costimulatory and other adhesion molecules that are upregulated by proinflammatory cytokines such as IL-1α, IL-1β, and TNF-α, thereby enhancing their ability to function as APC for Class II MHC restricted Th immune responses.

Macrophages and other mononuclear phagocytes are probably the most effective APC for antigens derived from most pathogenic microorganisms other than viruses through their ability to phagocytose large particles, such as bacteria and parasites. Under typical conditions, phagocytized microorganisms are then killed in the phagolysosomes and digested, resulting in the generation of antigenic fragments available for binding to Class II MHC molecules for presentation to Th cells. Other important mechanisms that allow macrophages to serve as effective APC include their ability to internalize soluble antigens through binding of antigen-antibody complexes to CD16, CD32 and CD64 receptors. Macrophages, also internalize complement coated proteins through receptors for C3 and other C' components and upon stimulation by growth factors, by macropinocytosis. Moreover, macrophages express receptors for mannose and are a major source of pro-inflammatory cytokines including IL-1α, IL-1β, IL-6, IL-8, IL-12, TNF-α, and TNF-β that exert potent immunoregulatory activities on T cell responses (Sztein et al, supra (1997)).

B lymphocytes are very effective APC for soluble antigens for presentation to Th cells. This is largely based on their ability to bind and internalize specific soluble antigens very efficiently through the B-cell receptor complex (BCR), consisting of the specific membrane immunoglobin (mIg) and the Iga (CD79α)-Igβ (CD79β) heterodimer (Falk et al, supra (1993)).

Langerhans cells (LC), derived from bone marrow progenitors, are considered to be the only cells present in the epidermis with APC capabilities. LC migrate out of the epidermis via the lymphatics to the regional lymph nodes where they develop into DC. Interestingly, LC express CD1, a nonclassical MHC molecule capable of presenting to T cells, in a restricted fashion, nonprotein antigens such as microbial lipid and glycolipid antigens.

The invention herein focuses on the antigen specific down-regulation of APC-mediated immune responses. The invention stems from the discovery of a macrophage surface receptor to which Zot binds in a specific and saturable way. The present invention describes a method for using Zot or zonulin as antigen-specific immunoregulators and in immunotherapeutics. Specifically, both Zot and zonulin inhibit APC-mediated antigen-specific lymphocyte proliferation in a dose dependent manner without affecting mitogen induced responses. This down-regulation of the immune response is at least in part associated with the decreased uptake of antigen.

Currently available modulators of immune responses, such as cyclosporin and steroidal compounds, have a generalized effect on antigen and mitogen stimulations of the immune system (Reed et al, *J. Immunol.*, 17:150–154 (1986)). The invention disclosed herein offers the advantage of enabling the down-regulation of immune responses to a particular antigen without inducing negative side effects, such as increased susceptibility to infection and generalized immune suppression, typical of the immunomodulators of the prior art.

SUMMARY OF THE INVENTION

It is a object of the invention to provide a method for down-regulating an animal host's immune response to certain antigens, thereby facilitating immune based therapies. Specifically, it is an object of the invention to inhibit the ability of antigen presenting cells (APC) to process and present antigens to lymphocytes, thereby suppressing the lymphocyte proliferation and subsequent immune system reactions in response to defined antigens.

It is a further object of the invention to provide a treatment for an animal afflicted with an autoimmune or immune related disease or disorder such as multiple sclerosis, rheumatoid arthritis, insulin dependent diabetes mellitus, celiac disease, Sjogren's syndrome, systemic lupus erythematsosus, auto-immune thyroiditis, idiopathic thrombocytopenic purpura, hemolytic anemia, Grave's disease, Addison's disease, autoimmune orchitis, pernicious anemia, vasculitis, autoimmune coagulopathies, myasthenia gravis, polyneuritis, pemphigus, rheumatic carditis, polymyositis, dermatomyositis, and scleroderma by administering an effective amount of a Zot-related immunoregulator. In an alternative embodiment, the treatment of the animal afflicted with an autoimmune or immune related disease or disorder may involve the administration of an effective amount of a Zot-related immunoregulator in combination with a specific auto-immune related antigen(s).

It is a further object of the invention to provide a treatment of an animal afflicted with immune rejection subsequent to tissue or organ transplantation by administering an effective amount of a Zot-related immunoregulator. In an alternative embodiment, the treatment of the animal afflicted with immune rejection subsequent to tissue or organ transplantation may involve the administration of an effective amount of a Zot-related immunoregulator in combination with a specific transplantation antigen(s).

It is a further object of the invention to provide a treatment for an animal afflicted with an inflammatory or allergic disease or disorder such as asthma, psoriasis, eczematous dermatitis, Kaposi's sarcoma, multiple sclerosis, inflammatory bowel disease, proliferative disorders of smooth muscle cells, and inflammatory conditions associated with mycotic, viral, parasitic, or bacterial infections by administering a therapeutically effective amount of a Zot-related immunoregulator. In an alternative embodiment, the treatment of the animal afflicted with an inflammatory or allergic disease or disorder may involve the administration of an effective amount of a Zot-related immunoregulator in combination with a specific inflammatory related antigen(s) or allergen (s).

BRIEF DESCRIPTION OF THE DRAWINGS

FIG. 5A depicts FITC-dextran uptake in media at 0° C. (2.9%) and represents the temperature dependence of antigen uptake. FIG. 5B depicts FITC-dextran uptake in media at 37°C (46.0%) and represents a control for antigen uptake. FIG. 5C depicts FITC-dextran uptake in BSA at 37° C. (39.0%) and represents a negative control of antigen uptake. FIG. 5D depicts FITC-dextran uptake in Zot at 37° C. (19.3%). The data show that Zot decreases the uptake of antigen.

FIG. 7C shows the kinetics of binding of anti-CD14-FITC to unlabeled human monocyte/macrophages. Data are presented as isometric displays of Zot-FITC intensity (y axis) versus time (x axis) versus cell number (z axis) for cells gated on CD3 (lymphocytes) or CD14 (macrophages). The results indicate that Zot binding to human macrophages (FIG. 7A) and lymphocytes (FIG. 7B) occurs very rapidly, reaching equilibrium within 2 min following addition of Zot-FITC.

DETAILED DESCRIPTION OF THE INVENTION

Figure 1:
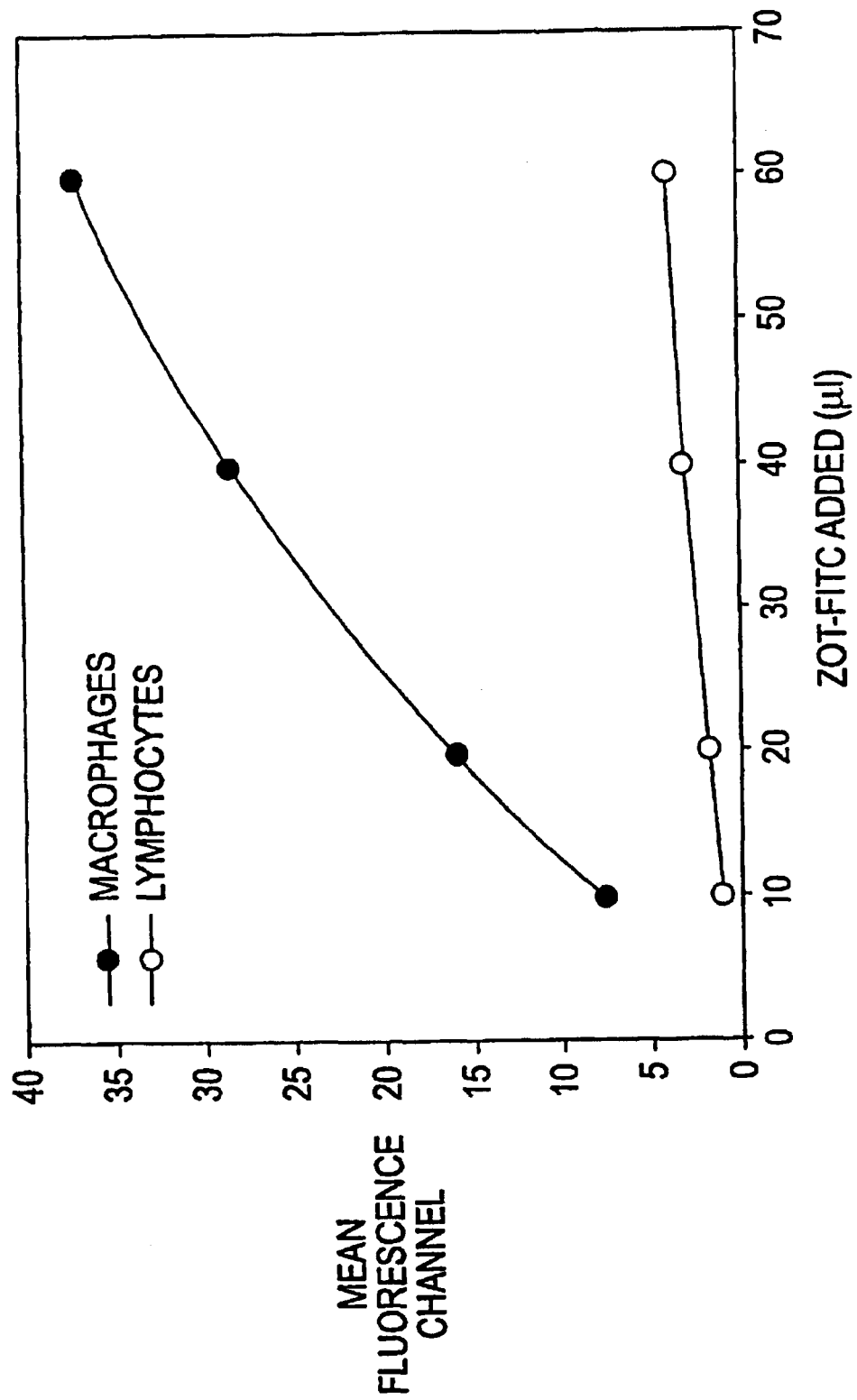
FIG. 1 illustrates Zot-FITC saturation binding curves for lymphocytes and macrophages. The data demonstrate that Zot binds preferentially to human monocytes/macrophages.

Previous studies have focused on the ability of Zot and zonulin to physiologically modulate the opening of mammalian tight junctions (or zonula occludens) of the epithelia of various tissues, such modulation particularly useful to facilitate drug delivery across these membranes. In the course of this study, receptors to Zot and zonulin were identified and isolated from CaCo2 cells, heart, intestinal and brain tissue. Further to the discovery of Zot receptors, peptide antagonists of zonulin were identified, said peptide antagonists binding to Zot receptor, yet not functioning to physiologically modulate the opening of mammalian tight junctions (i.e., lacking the biologic activity). The peptide antagonists competitively inhibit the binding of Zot and zonulin to the Zot receptor, thereby inhibiting the ability of Zot and zonulin to regulate the tight junctions.

In light of the known effect of Zot and zonulin on the paracellular pathway, it was indeed surprising to find a receptor for Zot on fully differentiated macrophages isolated from blood. It was initially unclear why circulating cells such as macrophages would have a receptor for a molecule associated with tissue cell modulation. In pursuing the answer to this question, it was discovered that Zot and zonulin also have the ability to physiologically regulate the activity of macrophages. Though not wishing to be bound by theory, it appears that Zot is blocking the receptor on the macrophage, binding to the macrophage surface receptor in a specific and saturable way. By binding to macrophages, Zot alters the macrophages ability to process and present an antigen to lymphocytes, ultimately suppressing the proliferation of lymphocytes in response to the antigen in a dose dependent and antigen-specific manner. In other words, Zot allows the antigen-specific down-regulation of an immune response. The results described in detail below further suggest that this down-regulation of the inimmune response is at least in part associated with the decreased uptake of antigen. It appears that Zot is a multi-functional protein, controlling the immune response by a dual mechanism of regulating the uptake and the trafficking of antigens.

Zonula occludens toxin or "Zot" is produced by *V. cholerae*. The particular strain of *V. cholera* from which Zot is derived is not critical to the present invention. Examples of such *V. cholerae* strains include strain 569B, 395 and E7946 (Levine et al, supra; Johnson et al, supra; and Karasawa et al, supra).

As used herein, "Zot" refers to the mature protein of 399 amino acids, as well as mutants thereof which retain the ability to regulate tj.

For example, an N-terminal deletion of amino acids 1–8 can be made without effecting Zot activity, and N-terminal fusion proteins of Zot can be made without effecting Zot activity. Such mutants can be readily prepared by site-directed mutagenesis, and screened for Zot activity as described herein.

Zot can be obtained and purified, e.g., by genetically-engineered *E. coli* strains over-expressing the zot gene (Baudry et al, *Infect. Immun.*, 60:428–434 (1992)), alone or fused to other genes, such as maltose binding protein (see Example 1 below), glutathione-S-transferase (see Example 2 below), or 6 poly-histidine (see Example 2 below).

As used herein, the term "zonulin" refers to a substantially pure biologically active protein having an apparent molecular weight of about 47 kDa, as determined by SDS-polyacrylamide gel electrophoresis, and the following N-terminal amino acid sequence: Asn Asp Gln Pro Pro Pro Ala Gly Val Thr Ala Tyr Asp Tyr Leu Val Ile Gln (SEQ ID NO:1), or the following N-terminal amino acid sequence: Glu Val Gln Leu Val Glu Ser Gly Gly Xaa Leu Val Gln Pro Gly Gly Ser Leu Arg Leu (SEQ ID NO:2) as well as mutants thereof which retain the ability bind to the receptor for Zot and to regulate tj.

Zonulin is produced by, or found in, various mammalian cells and tissues, e.g., rabbit or human cells/tissue. The particular mammalian cell/tissue type from which zonulin is derived is not critical to the present invention. Examples of such mammalian tissue types include heart, lung, intestine, liver, brain, kidney, and pancreas.

Zonulin can be obtained and purified, e.g., by affinity-purification chromatography using anti-ZOT antibodies, as described in Example 3 of U.S. Pat. No. 5,945,510, incorporated by reference herein.

As used herein, the terms "Zot-related immunoregulator" or "Zot-related immunoregulating molecule" refers to Zot or zonulin, as defined above. Furthermore, as used herein, the term "inhibition" (and "inhibit" and "inhibiting") refers to the down regulation of any aspect of APC activity that results in a substantial reduction of lymphocyte proliferation. Example activities include antigen uptake, antigen processing, and antigen presentation. The term "linhibition" as used herein does not necessarily imply complete suppression of function or result. Rather, partial inhibition is contemplated by the term.

To provide a treatment for an animal host afflicted with an autoimmune or immune related disease or disorder such as multiple sclerosis, rheumatoid arthritis, insulin dependent diabetes mellitus, celiac disease, Sjogren's syndrome, systemic lupus erythematsosus, auto-immune thyroiditis, idiopathic thrombocytopenic purpura, hemolytic anemia, Gravel's disease, Addison disease, autoimmune orchitis, pernicious anemia, vasculitis, autoimmune coagulopathies, myasthenia gravis, polyneuritis, pemphigus, rheumatic carditis, polymyositis, dermatomyositis, and scleroderma, a Zot-related immunoregulator is administered alone or in combination with a specific auto-immune related antigen. Examples of specific auto-immune antigens associated with auto-immune diseases or disorders are gliadin (antigen associated with celiac disease) and myelin basic protein (associated with multiple sclerosis).

To provide a treatment for an animal host afflicted with immune rejection subsequent to tissue or organ transplantation, a Zot-related immunoregulator is administered alone or in combination with a specific transplantation antigen. Transplantation antigens may be obtained by assaying for the HLA of the transplant tissue or organ.

To provide a treatment for an animal host afflicted with an inflammatory or allergic disease or disorder such as asthma, psoriasis, eczematous dermatitis, Kaposi's sarcoma, multiple sclerosis, inflammatory bowel disease, proliferative disorders of smooth muscle cells, and inflammatory conditions associated with mycotic, viral, parasitic, or bacterial infections, a Zot-related immunoregulator is administered alone or in combination with a specific inflammatory related antigen or allergen. Examples of specific inflammatory related antigens associated with inflammatory or allergic diseases or disorders are pollens and dust (associated with asthma), proteins found in cow's milk or fragments thereof (associated with eczematous dermatitis), myelin base protein (associated with multiple sclerosis) and vaccine antigens to the particular virus, parasite or bacteria associated with the inflammatory condition.

The present invention allows for the antigen-specific down-regulation of the immune response. As discussed above, one embodiment of the present invention involves the administration of an effective amount of a Zot-related immunoregulator (Zot or zonulin) alone or in combination with a specific antigen, the lymphocyte response to said antigen being specifically suppressed in a dose-dependent manner. It is clear from the results the details of which are presented herein that the present invention is limited to those antigens processed and presented by antigen presenting cells (APC) those requiring macrophage mediation. The invention relates to all APCs including macrophages and other mononuclear phagocytes, dendritic cells, B lymphocytes, Langerhans cells and human endothelial cells. In a preferred embodiment, the APC is a macrophage.

The present invention may be utilized both in vivo or in vitro environments. The only criticality is the administration to animal cells, said cells either in a living host or in a cell culture. Animal cells are defined as nucleated, non-chloroplast containing cells derived from or present in multicellular organisms whose taxonomic position lies within the kingdom animalia, a primary cell culture, explant culture or a transformed cell line.

The recipient or host animals employed in the present invention are not critical thereto and include cells present in or derived from all organisms within the kingdom animalia. In a preferred embodiment, the animal is within the family of mammals. Preferred animal and animal cells are mammal cells, such as humans, bovine, ovine, porcine, feline, buffalo, canine, goat, equine, donkey, deer and primates. The most preferred animal or animal cells are human or human cells.

The particular mode and method of administration is not critical to the invention. The only criticality is that both the Zot-related immunoregulating molecule and the antigen reach the macrophage intact. In the context of the present invention, the Zot-related immunoregulating molecule may be co-administered with the antigen. Alternatively, the two may be administered sequentially. For simplicity sake, discussion of mode of administration and pharmaceutical preparation below are directed to administration and preparation of the antigen. However, it is clear that the same modes apply to the administration of the Zot-related immunoregulating molecule. Furthermore, though the discussion is limited to administering a single antigen, it is clear that more than one antigen can be administered, the immune response to more than one antigen being subsequently down-regulated simultaneously.

Successful administration requires the delivery to an APC rich environment. Preferred administration routes include those that target sites of the immune system, such as the mucosa or the lymph tissues. Thus, intranasal, intraocular, intraintestinal, and intravaginal are preferred administration routes. This does not preclude that parenteral administration, such as intradermal, intramuscular, subcutaneous and intravenous, might also be effective routes of administration of Zot or zonulin, alone or in combination with the preferred antigen(s).

Depending on the particular administration route, the dosage form may be solid, semisolid, or liquid preparation. The dosage form may include: those additives, lubricants, stabilizers, buffers, coatings, and excipients as is standard in the art of pharmaceutical formulations.

Regarding the mode of administration, the antigen can be administered as oral dosage compositions for small intestinal delivery. Such oral dosage compositions for small intestinal delivery are well-known in the art, and generally comprise gastroresistant tablets or capsules (*Remington's Pharmaceutical Sciences*, 16th Ed., Eds. Osol, Mack Publishing Co., Chapter 89 (1980); Digenis et al, *J. Pharm. Sci.*, 83:915–921 (1994); Vantini et al, *Clinica Terapeutica*, 145:445–451 (1993); Yoshitomi et al, *Chem. Pharm. Bull.*, 40:1902–1905 (1992); Thoma et al, *Pharmazie*, 46:331–336 (1991); Morishita et al, *Drug Design and Delivery*, 7:309–319 (1991); and Lin et al, *Pharmaceutical Res.*, 8:919–924 (1991)); each of which is incorporated by reference herein in its entirety).

Tablets are made gastroresistant by the addition of, e.g., either cellulose acetate phthalate or cellulose acetate terephthalate.

Capsules are solid dosage forms in which the antigen is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a single antigen or a combination thereof at the exact dosage level considered best for the individual subject. The hard gelatin capsule consists of two sections, one slipping over the other, thus completely surrounding the antigen alone or in combination with the immunoregulating molecule. These capsules are filled by introducing the antigen, or gastroresistant beads containing the antigen, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the antigen from being significantly inactivated by gastric fluids in the stomach, thereby allowing the antigen to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized peptide antagonist in the aqueous buffering agent.

Likewise, other dosage delivery vehicles are contemplated by the present invention including but not limited to liposomes, cochleates, water soluble polymers and microspheres. The dosage composition may further include adjuvants such as monophosphoryl lipid A, QS-21, ISCOMs, and cytokines.

The antigen can also be administered as intravenous dosage compositions for delivery to the systemic elements of the immune system. Such compositions are well-known in the art, and compositions generally comprise a physiological ino diluent, e.g., distilled water, or 0.9% (w/v) NaCl. Likewise, the administration may be parenteral, intradermal, intramuscular, or subcutaneous and mentioned above. Dosage forms for such administration would clearly include pharmaceutically acceptable form, including physiologic buffers, diluents or the like.

As used herein, an effective amount of a Zot-related immunoregulator, such as Zot or zonulin, refers to an amount effective to down-regulate the activity of said antigen presenting cell, thereby being effective to down-regulate the antigen presenting cell-mediated lymphocyte proliferation. The specific amount of antigen and Zot-related immunoregulator molecule employed is not critical to the present invention and will vary depending upon the disease or condition being treated, as well as the age, weight and sex of the subject being treated. Generally, to achieve such a final concentration in, e.g., the intestines or blood, the amount of Zot-related immunoregulator molecule in a single oral dosage composition of the present invention will generally be about 0.1 μg to about 100 μg, preferably about 2.0 μg to about 60 μg, more preferably about 20 μg to about 50 μg. Likewise, the amount of antigen in a single oral dosage composition of the present invention will generally be in the range of about 0.01 μg to about 1000 μg, more preferably about 0.1 μg to about 100 μg. Obviously, the exact dosage of antigen will vary with the disease or disorder being treated, the preferred ranges being readily determinable through routine experimentation and optimization proceedings.

The following examples are provided for illustrative purposes only, and are in no way intended to limit the scope of the present invention.

EXAMPLE 1

Binding of FITC-labeled Zot to Lymhocytes and Macrophages

A. Materials and Methods

Isolation of Human Peripheral Blood Mononuclear Cells (PBMC) from Healthy Volunteers PBMC were isolated by density gradient centrifugation over lymphocyte separation media (LSM, Organon-Teknika, Durham, N.C.) from healthy volunteers. Donors were adults and gave informed consent for the blood drawing. PBMC used were fresh or were aliquoted and frozen in RPMI containing 10% (v/v) FCS and 10% (v/v) DMSO using a controlled linear rate freezer apparatus (1° C. per min, Planner Biomed, Salisbury, England) to preserve cell viability and maximize cell recovery. Cells were stored in liquid nitrogen until used. In some experiments, cells were used immediately after isolation.

Preinaration of Purified ZOT-MBP 5000 ml of the supernatant fraction obtained after culturing *V. cholerae* strain CVD110 (Michalski et al, *Infect. Immun.*, G1:4462–4468 (1993), which had been transformed with plasmid pZ14, was concentrated 1000-fold using a lamina flow filter with a MW cutoff of 10 kDa. The construction of pZ14, which contains the *Vibric cholera* zot gene, is described in detail in, inter alia, WO 96/37196. The resulting supernatant was then sujected to 8.0% (w/v) SDS-PAGE. Protein bands were detected by Coomassie blue staining of the SDS-PAGE gel. No protein band corresponding to Zot was detectable when compared to control supernatant f rom strain CVD110 transformed with plasmid pTTQ181 (Amersham, Arlington Heights, Ill.), and treated in the same manner. Therefore, even though the zot gene was placed behind the highly inducible and strong tac promoter in pZ14, the level of the protein in 1000-fold concentrated pZ14 supernatant was still not detectable by the Coomassie stained SDS-PAGE gel.

Hence, to increase the amount of Zot produced, the zot gene was fused in frame with the maltose binding protein (hereinafter "MBP") gene to create a MBP-ZOT fusion protein.

The MBP vector pMAL-c2 (Biolab) was used to express and purify Zot by fusing the zot gene to the mrale gene of *E. coli*. This construct uses the strong, inducible tac promoter, and the malE translation initiation signals to give high level expression of the cloned zot gene. The vector pMAL-c2 has an exact deletion of the malE signal sequence, which leads to cytoplasmic expression of the fusion protein. Affinity chromatography purification for MBP was used to facilitate isolation of the fusion protein (Biolab).

More specifically, vector pMAL-c2 was linearized with EcoRI (that cuts at the 3' end of the malE gene), filled in with Klenow fragment, and digested with XbaI (that has a single site in pMAL-c2 polylinker). The orf encoding ZOT was subcloned from plasmid pBB241 (Baudry et al, *Infect. Immun.*, 60:428–434 (1992)). Plasmid pBB241 was digested with BssHII, filled in with Klenow fragment, and digested with XbaI. Then, the blunt-XbaI fragment was subcloned into pMAL-c2 to give plasmid pLC10-c. Since both the insert, and the vector had blunt and sticky ends, the correct orientation was obtained with the 3' end of malE fused with the 5' terminus of the insert. pLC10-c was then electroporated into *E. coli* strain DH5a. In pBB241, the BsBHII restriction site is within the zot orf. Thus, amino acids 1–8 of ZOT are missing in the MBP-ZOT fusion protein.

In order to purify the MBP-Zot fusion protein, 10 ml of Luria Bertani broth containing 0.2% (w/v) glucose and 100 μg/ml ampicillin were inoculated with a single colony containing pLC10-c, and incubated overnight at 37° C. with shaking. The culture was diluted 1:100 in 1.0 ml of the same fresh medium, and grown at 37° C. while shaking, to about $1.0 \times 10^8$ cells/ml. 0.2 mM IPTG was then added to induce the MBP-Zot expression, and the culture was incubated at 37° C. for additional 3 hr. The bacteria were then pelleted and resuspended in 20 ml of ice cold "column buffer" comprising 20 mM Tris-HCl, 0.2 M NaCl, 1.0 mM EDTA, 10 mM 2-ME, 1.0 mM $NaN_3$. The bacterial suspension was lysed by french press treatment and spun for 30 min at 13,000×g at 4° C. The supernatant was collected, diluted 1:5 with column buffer and loaded into a 1×10 column of amylose resin (Biolabs, MBP-fusion purification system), pre-equilibrated with column buffer. After washing the column with 5 volumes of column buffer, the MBP-ZOT fusion protein was eluted by loading 10 ml of 10 mM maltose in column buffer. The typical yield from 1.0 ml of culture was 2–3 mg of protein.

The MBP fusion partner of the purified MBP-Zot fusion protein was then cleaved off using 1.0 μg of Factor Xa protease (Biolabs) per 20 μg of MBP-Zot. Factor Xa protease cleaves just before the amino terminus of Zot. The Zot protein so obtained was run on a 8.0% (w/v) SDS-PAGE gel, and electroeluted from the gel using an electroseparation chamber (Schleicher & Schuell, Keene, N.H.).

When tested in Ussing chambers, the resulting purified Zot induced a dose-dependent decrease of Rt, with an $ED_{50}$ of $7.5 \times 10^{-8}$ M.

Conjugation of ZOT-MBP to Fluorescein Isothiocyanate (ZOT-FITC)

Conjugation of Zot-MBP to FITC was performed following standard techniques. Briefly, Zot-MBP was dialyzed against 500 ml FITC labeling buffer comprising 0.1 M bicarbonate buffer (e.g., 0.09 M $NaHCO_3$+0.0085 M $Na_2CO_3$), adjusted to pH 9.0 with concentrated NaOH and stored at 4° C., at 4° C. for 8 hr to raise the pH to 9.0. Ten μl of 5.0 mg/ml FITC in DMSO for each milligram of MBP-ZOT was then added, followed by an overnight incubation in PBS at 4° C. Unbound FITC was then removed by dialysis in 500 ml dialysis buffer comprising PBS (pH 7.4), stored at 4° C., at 4° C. with two to three changes over 2 days. This preparation was stored at 4° C. until used.

Binding of PITC-ZOT to Human PBMC and Flow Cytometric Analysis

PBMC isolated as described above were incubated with increasing concentrations of Zot-FITC for 60 min at 37° C.

in siliconized tubes (to preclude the binding of macrophages to the test tube walls) in the presence of monoclonal antibodies to CD14 conjugated to phycoerythrin (PE) and to CD3 conjugated to ECD (energy coupled dye, a PE-Texas-Red conjugate). CD14 is a marker of human monocytes/ macrophages, while CD3 is a marker of T lymphocytes. The use of these fluorochromes (e.g., FITC, PE and ECD) allowed the simultaneous study of the binding of ZOT to monocytes/macrophages and T lymphocytes in mixed PBMC populations by 3-color flow cytometry. Cells were then washed twice with PBS (pH 7.2) containing 1.0% (w/v) BSA and 0.1% (w/v) NaAzide, and analyzed immediately by flow cytometry using an Epics Elite flow cytometer/cell sorter system.

In these experiments, fluorochrome-labeled mAbs of the same isotypes, but irrelevant specificity, were used as a controls. Platelets, erythrocytes (if any) and cell debris were excluded from analysis by setting an appropriate gate on the forward vs. 90% light scatter. parameters. Data was collected for each sample for over 10,000 cells. Data analysis was performed using the Epics Elite analysis package (Coulter) or the WinList list-mode analysis package (verity Software House, Topsham, Me.).

B. Results

A representative experiment showing the flow cytometric analysis of Zot-FITC binding to human T lymphocytes (CD3$^+$) and monocyte/macrophages (CD14$^+$) is shown in FIG. 1. The results show that binding of Zot-FITC, as evidenced by mean fluorescent intensity levels, is several fold higher in monocytes/macrophages than in T lymphocytes. Furthermore, addition of increasing amounts of Zot-FITC results in increased binding that start to level off after addition of 40–60 µl of Zot-FITC. These results indicate that Zot binds preferentially to human monocyte/macrophages.

Figure 2:
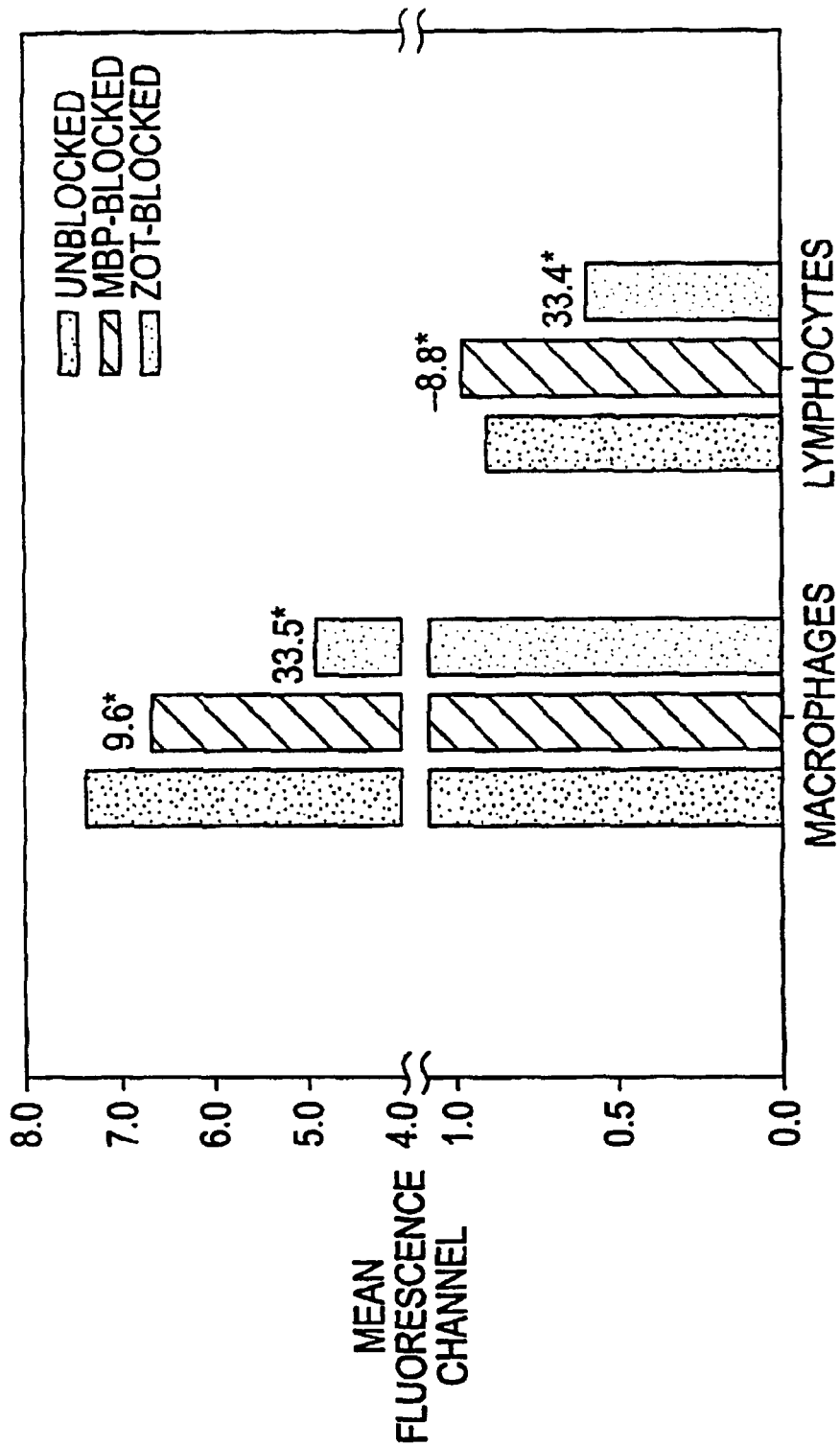
FIG. 2 illustrates blocking of Zot-FITC binding by unlabeled Zot. Preincubation of PBMC with unlabeled Zot decreased the binding of Zot-FITC to both, monocyte/macrophages and T lymphocytes by about 33%, suggesting that Zot binding to these cells is receptor-mediated. Preincubation of cells with purified MBP had no effect in blocking Zot-FITC binding, indicating that blocking with unlabeled Zot is a specific phenomenon.

Next, the binding of Zot-FITC to human monocyte/ macrophages and lymphocytes in the presence of unlabeled Zot was tested, to determine if the unlabeled Zot could block binding. As shown in FIG. 2, preincubation of PBMC for 30 min at 37° C. with 100 µl of unlabeled Zot, followed by the addition of ZOT-FITC (10 µl) for 30 min at 37° C., decreased by ~33% the binding of Zot-FITC to both, monocyte/macrophages and T lymphocytes, suggesting that Zot binding to these cells is receptor-mediated. Preincubation of cells with 100 µl of purified MBP, followed by the addition of ZOT-FITC (10 µl) for 30 min at 37° C., had no effect in blocking Zot-FITC binding, indicating that blocking with unlabeled Zot is a specific phenomenon.

EXAMPLE 2

Proliferative Responses to Mitogens and Antigens By Human Mononuclear Cells

A. Materials and Methods

Isolation of Human Peripheral Blood Mononuclear Cells (PBMC) From Healthy Volunteers PBMC were isolated by density gradient centrifugation over lymphocyte separation media (LSM, Organon-Teknika, Durham, N.C.) from healthy volunteers. In accordance with the institutional review board of University of Maryland, Baltimore, donors were adults and gave informed consent for the blood drawing. PBMC used were fresh or were aliquoted and frozen in RPMI containing 10% (v/v) FCS and 10% (v/v) DMSO using a controlled linear rate freezer apparatus (1° C. per min, Planner Biomed, Salisbury, England) to preserve cell viability and maximize cell recovery. Cells were stored in liquid nitrogen until used. In some experiments cells were used immediately after isolation.

Preparation of Purified Zot

The zot gene was amplified by PCR with Deep Vent polymerase (New England Biolabs), using pBB241 plasmid (Baudry et al, supra) DNA as a template. The forward and reverse primers used were: 5'-CGGGATCCCGTATGAGTATCTTT-3' (SEQ ID NO:3); and 5'-CCCAAGCTTGGGTCAAAATATACT-3' (SEQ ID NO:4), respectively. The 5' tails of these oligonucleotides contain a BamHI and a HindIII restriction site, respectively. The resulting amplicon (1.2 kb) was analyzed by 8.0% (w/v) agarose gel electrophoresis, and purified from salts and free nucleotides using an Xtreme spin column (Pierce). The above-noted two restriction enzymes were then used to digest the purified amplicon, and the resulting digested-amplicon was then inserted in the vector pQE30 (Quiagen), which had been previously digested with BamHI and HindIII, so as to obtain plasmid pSU113. pQE30 is an expression vector that provides high level expression of a recombinant protein with a 6 poly-histidine tag (6×His). The expression product of plasmid pSU113 is therefore a 6×His-Zot fusion protein. pSU113 was then transformed into E. coli DH5a.

In order to purify the 6×His-Zot fusion protein, the resulting transformed E. coli were grown overnight at 37° C. in 150 ml of Luria Bertani broth containing 2.0% (w/v) glucose, 25 µg/ml of kanamycin and 200 µg/ml of ampicillin until the A$_{600}$ was about 1.10. Next, 75 ml of the overnight cultures were added to 1000 ml of Luria Bertani broth containing 2.0% (w/v) glucose, 25 µg/ml of kanamycin and 200 µg/ml of ampicillin, incubated for about 3 hr at 37° C., with vigorous shaking, until the A$_{600}$ was about 0.7–0.9. Then, IPTG was added to a final concentration of 2.0 mM, and growth was allowed to continue for 5 hrs at 37° C. Next, the cells were harvested by centrifugation at 4000×g for 20 min, the cells resuspend in 5.0 ml/g wet weight of buffer A comprising 6.0 M GuHCl, 0.1 M sodium phosphate, and 0.01 M Tris-HCl (pH 8.0), and stirred for 1 hr at room temperature. Then, the mixture was centrifuged at 10,000×g for 30 min at 4° C., and to the resulting supernatant was added 4.0–5.0 ml/g wet weight of a 50% slurry of SUPERFLOW resin (QIAGEN), and stirring was carried out for 1 hr at room temperature. The resulting resin was loaded into a 1.6×8.0 column, which was then washed sequentially with buffer A, buffer B comprising 8.0 M urea, 0.1 M sodium phosphate, and 0.01 M Tris-HCl (pH 8.0) and buffer C comprising 8.0 M urea, 0.1 M sodium phosphate, and 0.01 M Tris-HCl (pH 6.3). Each wash was carried out until the A$_{600}$ of the flow-through was less than 0.01. The 6×His-ZOT fusion protein was eluted from the column using 20 ml of buffer C containing 250 mM imidazole. Then, the fractions containing with the 6×His-ZOT fusion protein were checked by SDS-PAGE using the procedure described by Davis, *Ann. N.Y. Acad. Sci.*, 121:404 (1964), and the gel stained with Comassie blue. The fractions containing 6×His-ZOT fusion protein were dialyzed against 8.0 M urea, combined, and then diluted 100 times in PBS. Next, 4.0 ml of a 50% slurry of SUPERFLOW resin was added, stirring was carried out for 2 hrs at room temperature, and the resulting resin loaded into a 1.6×8.0 column, which was then washed with 50 ml of PBS. The 6×His-Zot fusion protein was eluted from the column with 10 ml of PBS containing 250 mM imidazole. The resulting eluant was dialyzed against PBS, and the 6×His-ZOT fusion protein was checked by SDS-PAGE, as described above.

Preparation and Purification of Rabbit Anti-Zot Antiserum

To obtain specific antiserum, a chimeric glutathione S-transferase (GST)-Zot protein was expressed and purified.

More specifically, oligonucleotide primers were used to amplify the zot orf by polymerase chain reaction (PCR) using plasmid pBB241 (Baudry et al, supra) as template DNA. The forward primer (TCATCACGGC GCGCCAGG, SEQ ID NO:5) corresponded to nucleotides 15–32 of zot orf, and the reverse primer (GGAGGTCTAG AATCTGCCCG AT, SEQ ID NO:6) corresponded to the 5' end of ctxA orf. Therefore, amino acids 1–5 of ZOT were missing in the resulting fusion protein. The amplification product was inserted into the polyliriker (SmaI site) located at the end of the GST gene in PGEX-2T (Pharmacia, Milwaukee, Wis.). pGEX-2T is a fusion-protein expression vector that expresses a cloned gene as a fusion protein with GST of *Schistosoma japonicum*. The fusion gene is under the control of the tac promoter. Upon induction with IPTG, derepression occurs and GST fusion protein is expressed.

The resulting recombinant plasmid, named pLC11, was electroporated in *E. coli* DH5α. In order to purify GST-Zot fusion protein, 10 ml of Luria Bertani broth containing 100 μg/ml ampicillin were inoculated with a single colony containing pLC11, and incubated overnight at 37° C. with shaking. The culture was diluted 1:100 in 1.0 ml of the same fresh medium and grown at 37° C. while shaking, to about $1.0 \times 10^8$ cells/ml. 0.2 MM IPTG was then added to induce the GST-Zot expression, and the culture was incubated at 37° C. for additional 3 hr. The bacteria were then pelleted, resuspended in 20 ml of ice cold PBS (pH 7.4), and lysed by the french press method. The GST-Zot fusion protein was not soluble under these conditions as it sedimented with the bacterial pellet fraction. Therefore, the pellet was resuspended in Laemli lysis buffer comprising 0.00625 M Tris-HCl (pH 6.8), 0.2 M 2-ME, 2.0% (w/v) SDS, 0.025% (w/v) bromophenol blue and 10% (v/v) glycerol, and subjected to electrophoresis on a 8.0% (w/v) PAGE-SDS gel, and stained with Coomassie brilliant blue. A band of about 70 kDa (26 kDa of GST+44 kDA of Zot), corresponding to the fusion protein, was electroeluted from the gel using an electroseparation chamber (Schleicher & Schuell, Keene, N.H.).

10 μg of the resulting eluted protein (10–20 μg) was injected into a rabbit mixed with an equal volume of Freund's complete adjuvant. Two booster doses were administered with Freund's incomplete adjuvant four and eight weeks later. One month later the rabbit was bled.

To determine the production of specific antibodies, $10^{-10}$ M of Zot, along with the two fusion proteins MBP-Zot and GST-Zot, was transferred onto a nylon membrane and incubated with a 1:5000 dilution of the rabbit antiserum overnight at 4° C. with moderate shaking. The filter was then washed 15 min 4 times with PBS containing 0.05% (v/v) Tween 20 (hereinafter "PBS-T"), and incubated with a 1:30,000 dilution of goat anti-rabbit IgG conjugated to horseradish peroxidase for 2 hr at room temperature. The filter was washed again for 15 min 4 times with PBS containing 0.1% (v/v) Tween, and imtnunoreactive bands were detected using enhanced chemiluminescence (Amersham).

On immunoblot, the rabbit antiserum was found to recognize Zot, as well as MBP-Zot and GST-Zot fusion proteins, but not the MBP negative control.

Moreover, to confirm the production of ino appropriate anti-Zot antibodies, neutralization experiments were conducted in Ussing chambers. When pre-incubated with pZ14 supernatant at 37° C. for 60 min, the Zot-specific antiserum (1:100 dilution), was able to completely neutralize the decrease in Rt induced by Zot on rabbit ileum mounted in Ussing chambers.

Next, the anti-Zot antibodies were affinity-purified using an MBP-Zot affinity column. More specifically, a MBP-Zot affinity column was prepared by immobilizing, overnight at room temperature, 1.0 mg of purified MBP-Zot, obtained as described in Example 1 above, to a pre-activated gel (Aminolink, Pierce). The column was washed with PBS, and then loaded with 2.0 ml of anti-ZOT rabbit antiserum. After a 90 min incubation at room temperature, the column was washed with 14 ml of PBS, and the specific anti-Zot antibodies were eluted from the column with 4.0 ml of a solution comprising 50 mM glycine (pH 2.5), 150 mM NaCl, and 0.1% (v/v) Triton X-100. The pH of the 1.0 ml eluted fractions was immediately neutralized with 1.0 N NaOH.

Culture Conditions and Lympmhoproliferation Assays

PBMC ($1.5 \times 10^6$ cells/ml) were cultured in 1.0 ml of complete medium, (cRPMI) comprising RPMI 1640 containing 10% (v/v) fetal calf serum and 50 μg/ml gentamicin. Cells were incubated at 37° C., 5% $CO_2$ in 96-well plates in the absence or presence of phytohemagglutinin (PHA, a nonspecific mitogen, used at 2.0 μg/ml) or tetanus toxoid (TT; a specific antigen, used at 2.0 μg/ml; Connaught, Swift Water, Pa.) without or with purified ZOT (used at 20 or 60 μg/ml) or bovine serum albumin (BSA; a control protein, used at 20 or 60 μg/ml; Fraction V, Sigma, St. Louis, Mo.). In some experiments, an anti-ZOT rabbit antiserum or normal rabbit serum was also added to the cultures at initiation. Cells were cultured for 2 days (for PHA) or 6 days (for TT) and 1.0 μCi/ well of tritiated thymidine was added. Plates were harvested 20 hr later on a Wallac cell harvester (Gaithersburg, Md.) and incorporated thymidine measured on a Wallac Trilux Microbeta counter (Gaithersburg, Md.).

B. Results

Figure 3:
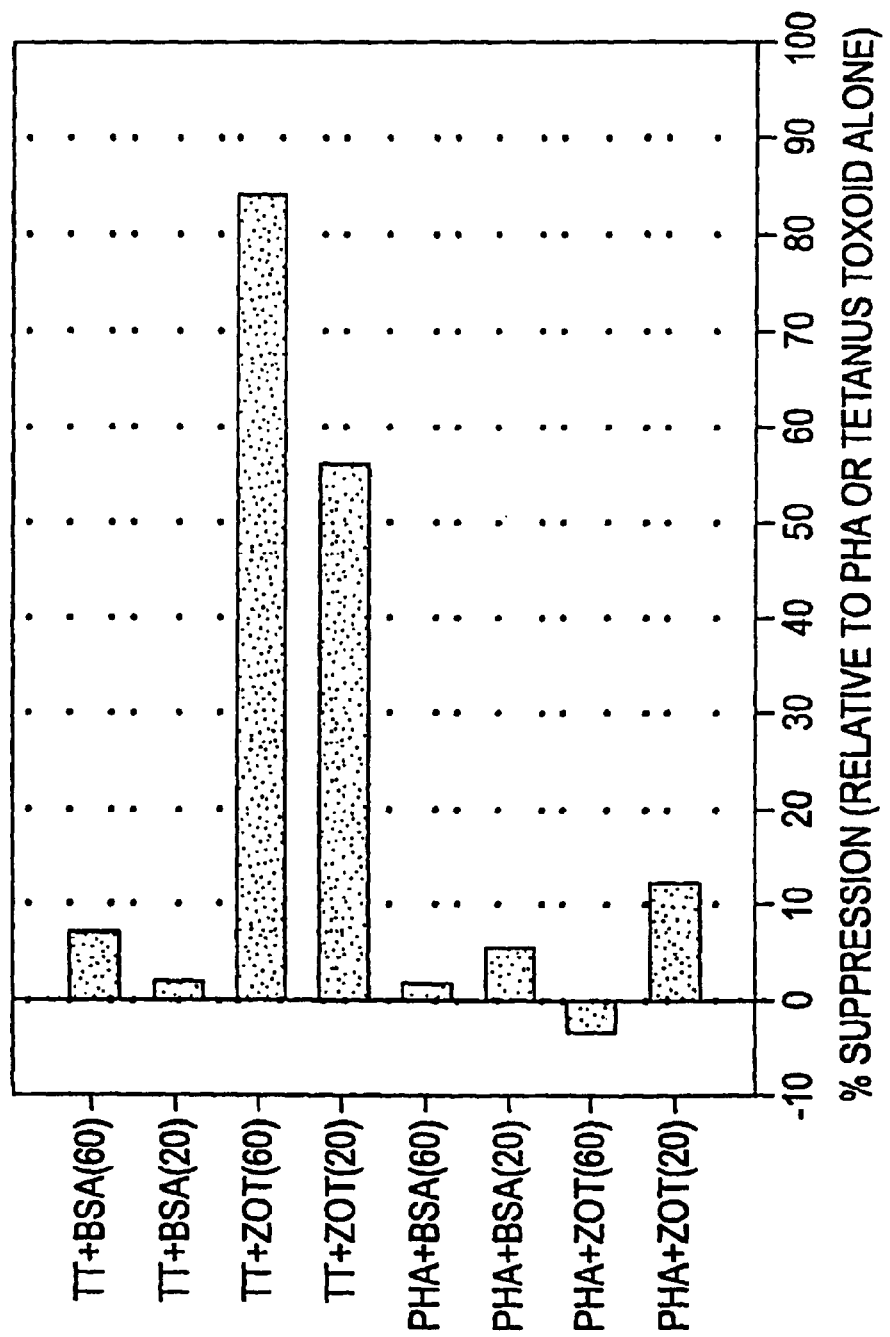
FIG. 3 illustrates the effects of Zot on proliferation of human PBMC induced by PHA and tetanus toxoid. The data demonstrate that Zot markedly suppresses tetanus toxoid-induced proliferation in a dose dependent manner while having no effect on PHA induced proliferation

A representative experiment showing the effects of purified Zot on proliferation of human PBMC induced by PHA and tetanus toxoid is shown in FIG. 3. The results clearly indicate that incubation with Zot markedly suppressed tetanus toxoid-induced proliferation (~85% at 60 μg/ml), while it had no effect on PHA-induced proliferation. Moreover, suppression of TT-induced proliferation by Zot appears to be dose-dependent. Significantly higher levels of suppression were observed when Zot was added at 60 μg/ml (~85%) than when 20 μg/ml Zot were used (~56% suppression). Addition of BSA, used as control protein has no effect on either TT or PHA-induced lymphocyte proliferation demonstrating the specificity of Zot biological activity.

Figure 4:
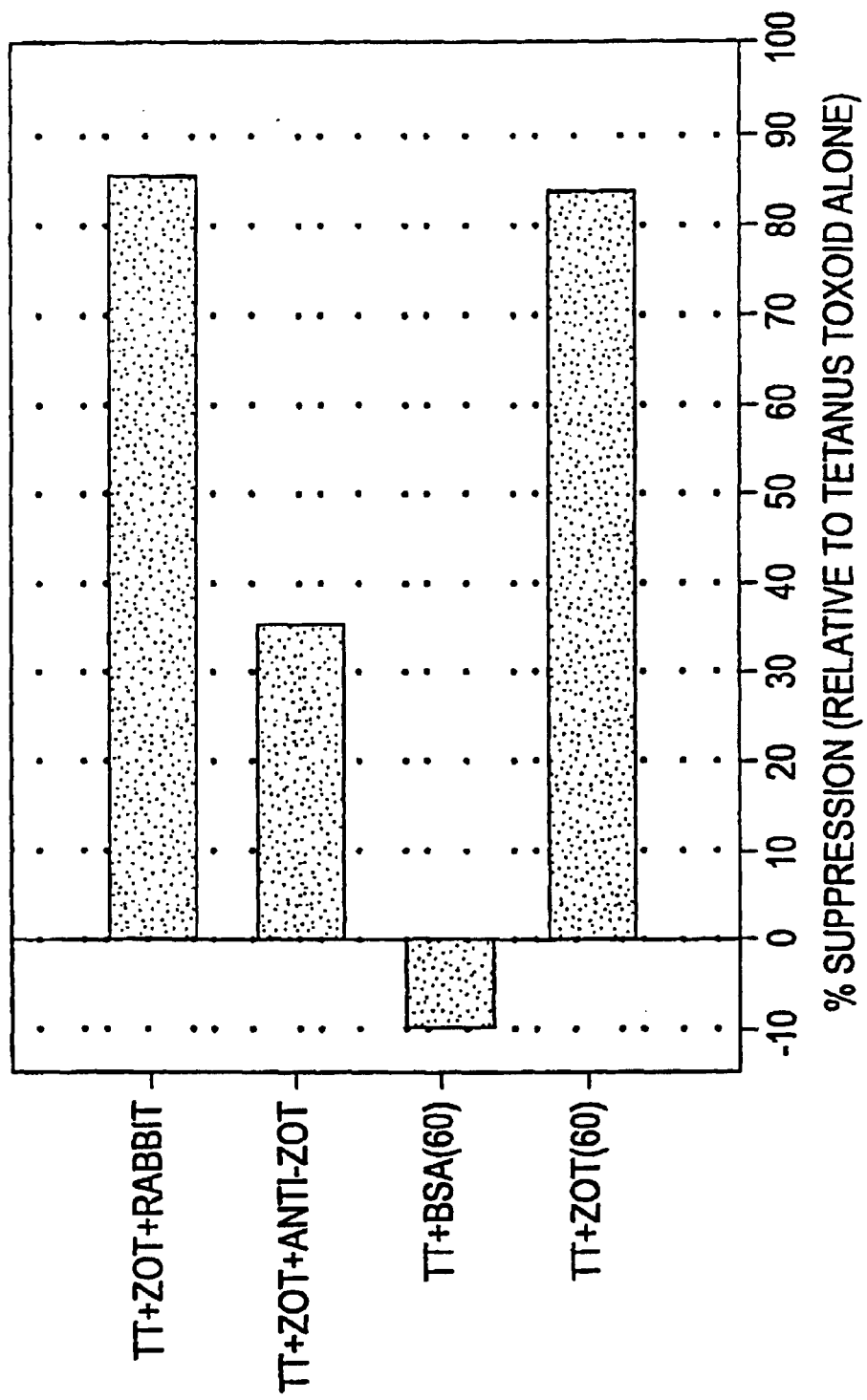
FIG. 4 illustrates the effects of anti-Zot antiserum on Zot-induced suppression of proliferation of human PBMC induced by tetanus toxoid. Addition of anti-Zot reverses the Zot-mediated suppression of tetanus toxin-induced proliferation by greater than 50%.
Figure 5A:
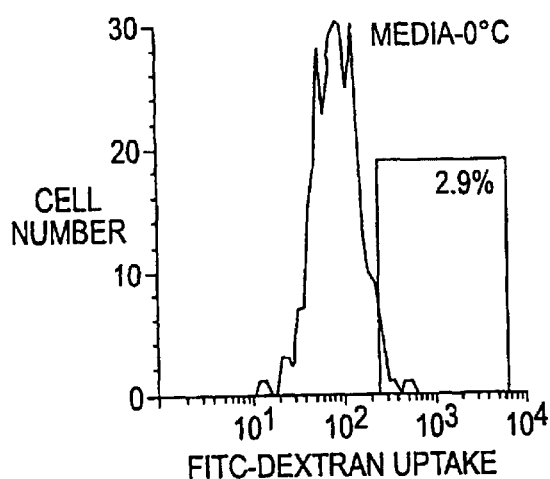
FIGS. 5A–5D illustrates the effect of Zot on FITC-dextran uptake by normal human CD14+HLA-DR+ macrophages.
Figure 5B:
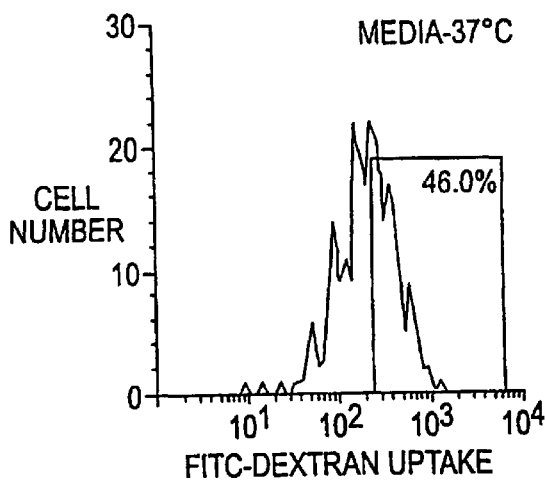
Figure 5C:
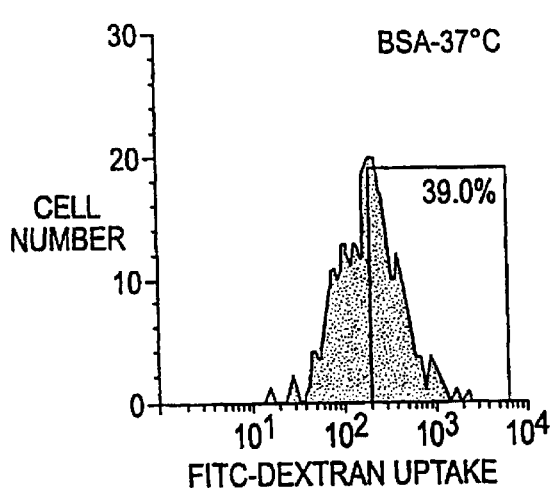
Figure 5D:
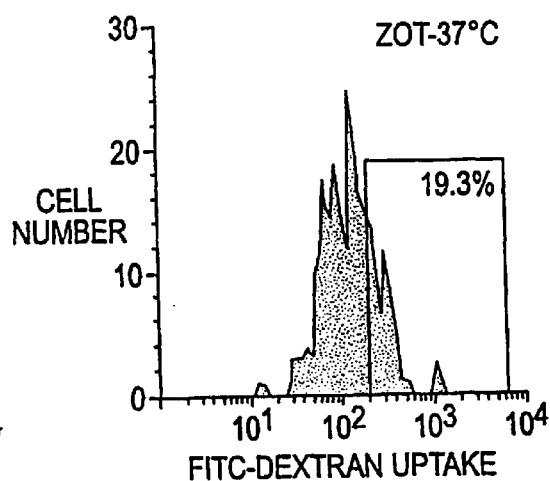

To further examine the specificity of Zot-induced suppression of TT-induced proliferation, llu PBMC were incubated in the absence or presence of TT with ZOT alone, ZOT+anti-ZOT rabbit antiserum (used at a 1:10 dilution) or Zot+normal rabbit serum (used at a 1:10 dilution). As can be observed in FIG. 4, addition of an anti-Zot rabbit antiserum reversed by greater than 50% Zot-mediated suppression of TT-induced proliferation. Addition of normal rabbit serum had no effect, confirming the specificity of Zot-mediated effects. Similarly, addition of BSA had no effect in this system.

EXAMPLE 3

Effects of Zot on FITC-Dextran Uptake by Human Monocytes and Macrophages

A. Materials and Methods

Isolation of Human Peripheral Blood Mononuclear Cells (PBMC) from Healthy Volunteers PBMC were isolated by density gradient centrifugation over lymphocyte separation media (LSM, Organon-Teknika, Durham, N.C.) from healthy volunteers. In accordance with the institutional review board of University of Maryland, Baltimore, donors were adults and gave informed consent for the blood drawing. PBMC used were fresh or were aliquoted and frozen in RPMI containing 10% (v/v) FCS and 10% (v/v) DMSO using a controlled linear rate freezer apparatus (1° C. per min, Planner Biomed, Salisbury, England) to preserve cell viability and maximize cell recovery. Cells were stored in liquid nitrogen until used.

Preparation of Purified 6xHis-Zot

The 6xHis-Zot fusion protein was prepared and purified by the process described above in Example 2 above.

Soluble Antigen Uptake

The ability to take up soluble antigen was measured using fluorescein isothiocyanate (FITC)-conjugated dextran (MW 50,700; Sigma). Freshly isolated PBMC (500,000 cells in 0.5 ml of cRPMI containing 10% (v/v) heat-inactivated FCS and 50 µg/ml of gentamicin) were incubated in the absence or presence of purified Zot (40 µg/ml) or BSA (40 µg/ml) for 3 hr at 37° C. in a final volume of 0.5 ml/50 ml tube. This incubation was performed under agitation in siliconized tubes to prevent the adherence of monocytes/macrophages to the tube walls. Following this incubation, FITC-dextran (at a final concentration of 300 µg/ml), as well as anti-CD14 allophycocyanin (APC)-labeled and anti-HLA-DR Peridinin Chlorophyll Protein(PerCP)-labeled monoclonal antibodies were added to each culture without washing and cells allowed to incubate for 30 min at 37° C. or on ice. Since uptake of FITC-dextran, and soluble antigens in general, depends on pinocytosis, a temperature-dependent phenomenon, incubations at 0° C. are performed to establish the levels of nonspecific binding of FITC-dextran to the cells.

In these experiments CD14 and HLA-DR (a major histocompatibility complex Class II antigen whose level of expression increase with cell activation) were used to identify monocyte/macrophages.

Cells were then washed once with ice cold PBS and run immediately on a Coulter Epics Elite flow cytometer/cell sorter system (Coulter Corp., Miami, Fla.). Analysis was performed using the WinList software package (Verity Software House, Topham, Me.). The percentages of cells that incorporated FITC-dextran were obtained by subtracting the percentage of cells that incorporated FITC-dextran at 0° C. (ice) from the percentage of cells that incorporated FITC-dextran at 37° C.

B. Results

A representative experiment showing the effects of Zot on FITC-dextran uptake by normal human CD14+ HLA-DR+ monocyte/macrophages is shown in FIGS. 5A–5D. The results show that Zot (FIG. 5D) markedly suppressed (~51–58%) FITC-dextran uptake by human monocyte/macrophages as compared to that observed in cells incubated with media alone or BSA. No significant differences were observed between the percentage of cells that incorporated FITC-dextran in media or in the presence of BSA. Moreover, as expected, incubation at 0° C. totally abrogated FITC-dextran uptake, confirming that this phenomenon is temperature-dependent.

It is well established that antigen uptake by APCs, such as monocyte/macrophages, is a critical event leading to lymphocyte activation and proliferation (Sztein et al, supra (1997)). The results showing that Zot interferes with FITC-dextran uptake demonstrate that the immunoregulatory effects of Zot on TT-induced proliferation are mediated, at least in part, by decreasing the ability of monocyte/macrophages to uptake antigen, leading to alterations in antigen processing and presentation. This is further supported by the fact that Zot does not affect PHA-induced proliferation, a phenomenon that does not require antigen processing and presentation.

EXAMPLE 4

Measurements of the Number of FITC-Zot Binding Sites/Cell in Human Monocytes/Macrophages and Lymphocytes A. Material and Methods Isolation of Human Peripheral Blood Mononuclear Cells (PBMC) From Healthy Volunteers PBMC were isolated by density gradient centrifugation over lymphocyte separation media (LSM, Organon-Teknika, Durham, N.C.) from healthy volunteers. In accordance with the institutional review board of University of Maryland, Baltimore, donors were adults and gave informed consent for the blood drawing. PBMC were aliquoted and frozen in RPMI containing 10% (v/v) FCS and 10% (v/v) DMSO using a controlled linear rate freezer apparatus (1° C. per min, Planer Biomed, Salisbury, England) to preserve cell viability and maximize cell recovery. Cells were stored in liquid nitrogen until used. In some experiments, cells were used immediately after isolation.

Preparation of Purified 6xHis-Zot

The preparation of 6xHis-Zot was as described in Example 2 above.

Conjugation of Zot to Fluorescein Isothiocyanate (Zot-FITC)

Conjugation of Zot with FITC was performed following standard, techniques. Briefly, Zot was dialyzed against 500 ml FITC labeling buffer comprising 0.05 M boric acid, 0.2 M MaCl, adjusted to pH 9.2 with concentrated NaOH, and stored at 4° C., at 4° C. overnight to remove free $NH_4^+$ ions and raise the pH to 9.2. 20 µl of 5.0 mg/ml FITC in DMSO for each milligram of Zot was then added, followed by an incubation for 2 hr at room temperature. Unbound FITC was then removed by dialysis in 500 ml dialysis buffer comprising 0.1 M Tris-HCl (pH 7.4), 0.1% (w/v) $NaN_3$, 0.2 M NaCl, adjusted to pH to 7.4 with concentrated NaOH, and stored at 4° C., at 4° C. with two to three changes over 2 days. This preparation was stored at 4° C. until used.

Binding of FITC-Zot to Human PBMC and Flow Cytometric Analysis

PBMC isolated as described above were incubated with increasing concentrations of Zot-FITC for 30 min at 37° C. in siliconized tubes (to preclude the binding of macrophages to the test tube walls) in the presence of monoclonal antibodies (mAb) to CD14 conjugated to phycoerythrin (PE) and to CD3 conjugated to ECD (energy coupled dye, a PE-Texas-Red conjugate). CD14 is used as a marker of human macrophages while CD3 is used as a marker for T lymphocytes. The use of these fluorochromes (e.g., FITC, PE and ECD) allowed us to study simultaneously the binding of Zot to macrophages. and T lymphocytes in mixed PBMC populations by 3-color flow cytometry. Following staining, cells were washed twice with PBS (pH 7.2) containing 1.0% (w/v) BSA and 0.1% (w/v) NaAzide and analyzed immediately by flow cytometry using an Epics Elite flow cytometer/cell sorter system (Beckman-Coulter, Miami, Fla.). In these experiments, fluorochrome-labeled mAbs of the same isotypes, but irrelevant specificity, were used as a controls. Platelets, erythrocytes (if any) and cell debris were excluded from analysis by setting an appropriate gate on the forward vs. 90% light scatter parameters. For each sample we collected data for over 10,000 cells. Data analysis was performed using the Epics Elite analysis package (Coulter) or the WinList list-mode analysis package (Verity Software House, Topsham, Me.). The amounts (in pM) of Zot-FITC added to each tube was derived from the final concentrations added (in μg/ml) and the known MW of Zot (44,900).

Calculation of Zot Binding Sites/Cell

The mean fluorescence intensity of each population following incubation with Zot-FITC were converted to number of Zot binding sites/cell using a standard curve constructed using the Quantum 26 MESF kit (range 10,000 to 500,000 MESF) and the QuickCal calibration software according to the manufacturers recommendations (Flow Cytometry Standards Corporation, San Juan, Puerto Rico). The fluorescent standards in the Quantum kit are calibrated in Molecules of Equivalent Soluble Fluorochrome (MESF) units against solutions of purified fluorescent dyes. The number of binding sites per cell (macrophages or lymphocytes) was derived from MESF units of Zot-FITC incubated samples (with non-specific binding, i.e., MESF of FITC-labeled mouse IgG controls, subtracted) adjusted for the fluorescein/protein ratio (F/P) of the various FITC-Zot batches used.

B. Results

Figure 6:
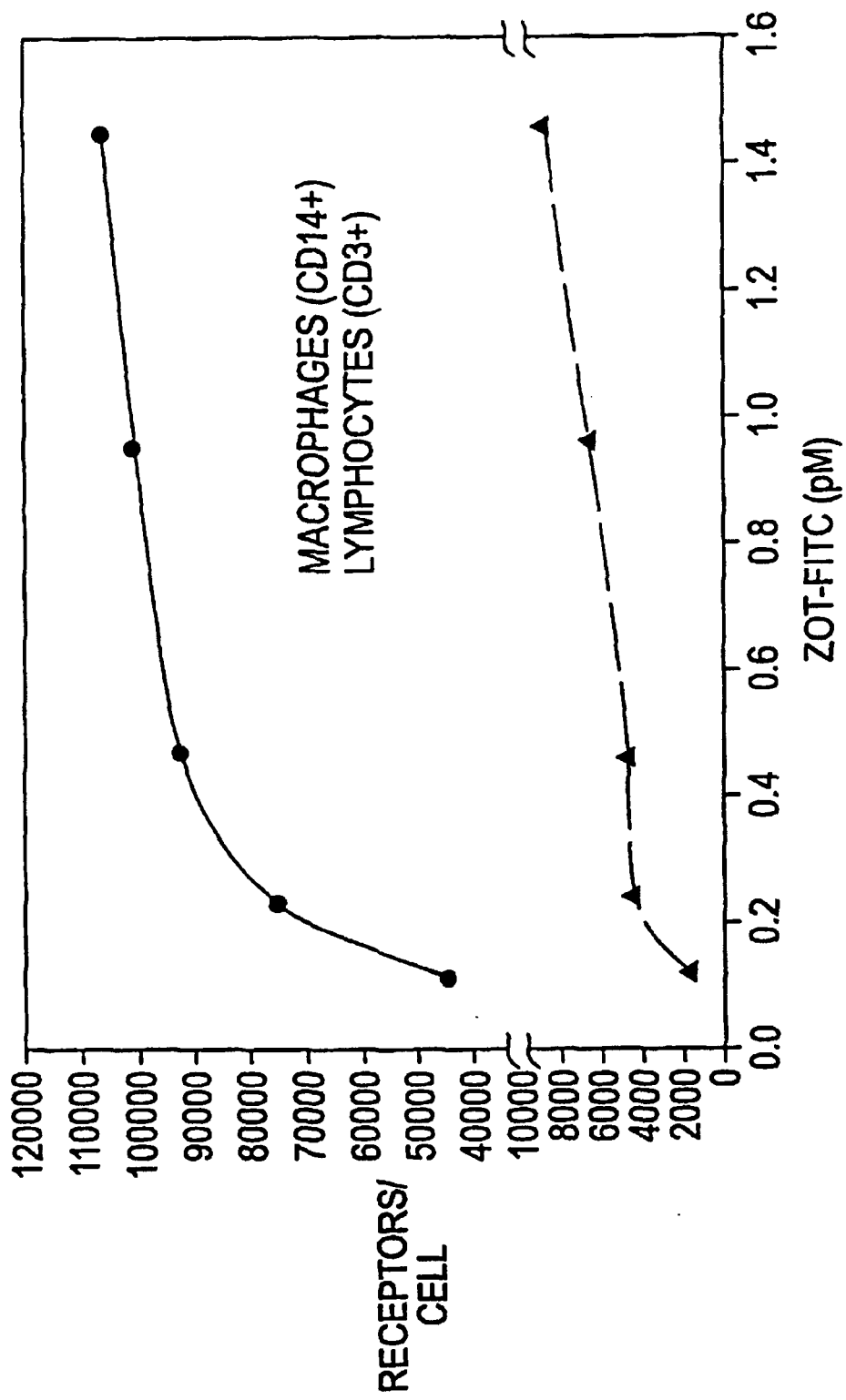
FIG. 6 illustrates the number of FITC-Zot binding sites/cell in human macrophages and lymphocytes. PBMC were incubated with increasing concentrations of Zot-FITC and analyzed by flow cytometry. The mean fluorescence intensity of each population following incubation with Zot-FITC were converted to number of Zot binding sites/cell using a standard curve constructed using the Quantum 26 MESF kit. These data show that binding of Zot is a saturable phenomenon, with saturation reached at approximately 0.5 pM and that the average number of Zot binding sites/cell is approximately 10-fold higher in macrophages (~106,000) than in lymphocytes (~9,000).

A representative experiment showing the flow cytometric analysis of Zot-F ITC binding to human T lymphocytes (CD3$^+$) and macrophages (CD14$^+$) is shown in FIG. 6. The results show that binding of Zot-FITC, as evidenced by increased number of Zot binding sites/cell, is several fold higher in macrophages, than in CD3$^+$ T lymphocytes. Furthermore, these data show that binding of Zot is a saturable phenomenon, with saturation reached at approximately 0.5 pM (~40 g/ml). Moreover, we observed that under saturation conditions, there are ~106,000 Zot-binding sites/cell and ~9,000 Zot-binding sites/cell in human macrophages and lymphocytes, respectively.

In order to explore the distribution of Zot binding sites in human macrophages and lymphocytes, the methodology described above was used to determine the number of Zot binding sites/cell in several volunteers. The results indicated that the average number of Zot binding sites/cell is, on average, approximately 10-fold higher in macrophages (mean=104,649; range=56,791–142,840) than in lymphocytes (mean=10,684; range=4,802–18,662).

EXAMPLE 5

Kinetics of Zot Binding to Human Monocytes/Macrophages and Lymphocytes

A. Material and Methods

Isolation of Human Peripheral Blood Mononuclear Cells (PBMC) From Healthy Volunteers PBMC were isolated from healthy volunteers as described above in Example 4.

Preparation of Purified 6xHis-Zot

The preparation of 6xHis-Zot was as described in Example 2 above.

Conjugation of Zot to Fluorescein Isothiocyanate (Zot-FITC)

Conjugation of Zot with FITC was as performed in Example 4 above.

Kinetics of Binding Assays

Determination of the kinetics of binding of Zot to human cells was carried out by flow cytometry using Zot-FITC conjugates and flow cytometry. Samples were run in real time using an EPIC ELITE flow cytometry/cell sorter system (Beckman-Coulter, Miami, Fla.). PBMC were stained with anti-CD3 mAb tagged with ECD (energy-coupled dye) and anti CD-14 mAb tagged with PE (phycoerythrin). Controls for background fluorescence were prepared with an additional aliquot of each cell suspension substituting irrelevant mAb of the same isotypes, conjugated with the corresponding fluorescent dyes, for the experimental mAb. PBMC labeled with anti-CD3 and anti-CD14 mabs were then washed and maintained in an ice bath until analyzed (within 1 hr) to minimize antigen modulation. Before analysis, cells were allowed to equilibrate at 37° C. for 15–20 min in a water bath and maintained at 37° C. using a viable sample handler (kinetics module, Cytek, Fremont, Calif.) attached to the flow cytometer for the duration of the experiment (12 min) while data was continuously collected. Baseline FITC fluorescence levels were collected for 90–150 seconds and data acquisition was paused for ~10–15 sec to inject Zot-FITC (to a final concentration of 40 μg/ml). Data collection was resumed immediately after the addition of Zot-FITC at a rate of ~300–600 cells/sec for a total of 12 min. FITC, PE and ECD-fluorochrome were excited using an air-cooled argon laser (488 nm emission). Results were calculated and displayed using the WinList and Isocontour analysis packages (Verity Software House, Topsham, Me.). Data are presented as isometric displays of Zot-FITC intensity (y axis) versus time (x axis) versus cell number (z axis) for cells gated on CD3 (T lymphocytes) or CD14 (macrophages).

B. Results

Figure 7A:
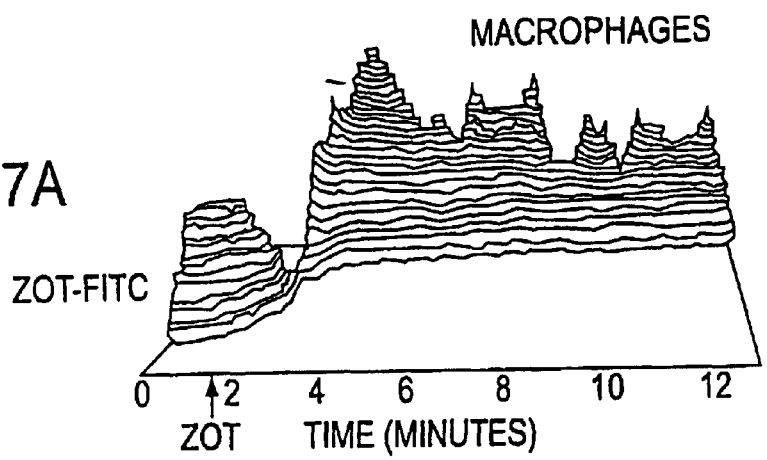
FIGS. 7A–7C illustrate the kinetics of Zot binding to human macrophages and lymphocytes. Determination of the kinetics of binding of Zot to human cells was carried out by flow cytometry using Zot-FITC conjugates. PBMC labeled with anti-CD3-ECD and anti CD-14-PE mAb were maintained at 37° C. for the duration of the experiment (12 min) while data was collected using a viable sample handler (kinetics module) attached to the flow cytometer. Baseline FITC fluorescence levels were collected for 90–150 seconds (indicated by the arrows) and data acquisition was paused for ~10–15 sec to inject Zot-FITC (FIGS. 7A and 7B).
Figure 7B:
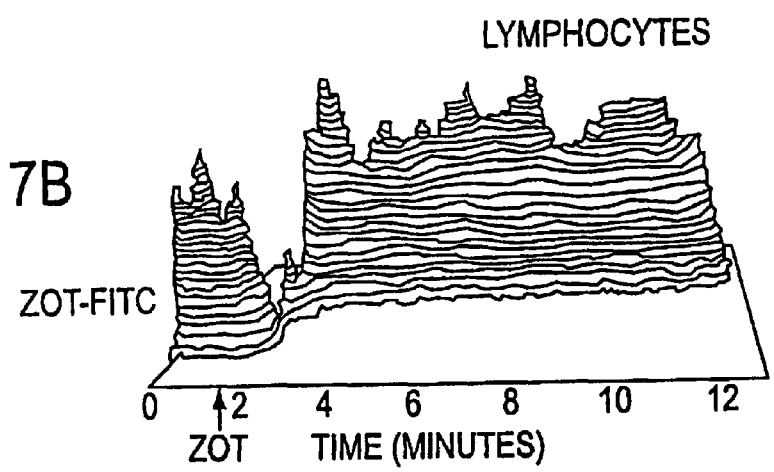
Figure 7C:
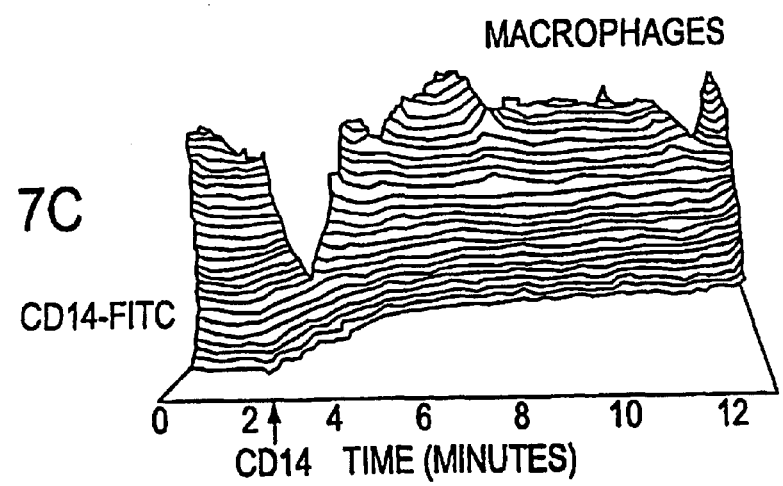

A representative experiment showing the kinetics of Zot-F ITC binding to human T lymphocytes (CD3$^+$) and macrophages (CD14$^+$) is shown in FIGS. 7A–7C. The results indicate that Zot binding to human macrophages (FIG. 7A) and lymphocytes (FIG. 7B) occurs very rapidly, reaching equilibrium within 2 min following addition of Zot-FITC. To compare the time required for Zot and an anti-CD14 mAb to reach maximum binding, similar experiments were performed using unlabeled cells. In these experiments, baseline FITC fluorescence levels were collected as described above, data acquisition was paused for ~10–15 sec to inject FITC-anti-CD14 mAb and data collection resumed immediately for a total of 12 min. The results (FIG. 7C) indicate that maximum levels of Zot binding occur in less time (~2 min) than that required by anti-CD14 mAb to reach equilibrium (~5 min).

EXAMPLE 6

Binding of FITC-Zot to Human B and T Lymphocytes

A. Material and Methods

Isolation of Human Peripheral Blood Mononuclear Cells (PBMC) From Healthy Volunteers PBMC were isolated from healthy volunteers as described in Example 4 above.

Preparation of Purified 6xHis-Zot

The preparation of 6xHis-Zot was as described in Example 2 above.

Conjugation of Zot to Fluorescein Isothiocyanate (Zot-FITC)

Conjugation of Zot with FITC was as performed in Example 4 above.

Binding of FITC-Zot to Human PBMC and Flow Cytometric Analysis

PBMC isolated as described above were incubated with 40 μg/ml of Zot-FITC for 30 min at 37° C. in the presence of mAb to CD14 conjugated to PE, CD3 conjugated to Tricolor (a PE-Cy5 conjugate) and anti-CD19 conjugated to ECD (energy coupled dye, a PE-Texas-Red conjugate). CD14 is a marker of human macrophages, CD3 is a marker of T lymphocytes and CD19 is a marker for B lymphocytes. The use of these fluorochromes (e.g., FITC, PE, TC and ECD) allowed us to study simultaneously the binding of Zot to macrophages, T and B lymphocytes in mixed PBMC populations by 4-color flow cytometry. Following staining cells were washed twice with PBS (pH 7.2) containing 1.0% (w/v) BSA and 0.1% (w/v) NaAzide and analyzed immediately by flow cytometry using an Epics Elite flow cytometer/cell sorter system (Beckman-Coulter, Miami, Fla.). In these experiments, fluorochrome-labeled mAbs of the same isotypes, but irrelevant specificity, were used as a controls. Platelets, erythrocytes (if any) and cell debris were excluded from analysis by setting an appropriate gate on the forward vs. 90% light scatter parameters. For each sample, data for over 10,000 cells was collected. Data analysis was performed using the Epics Elite analysis package (Coulter) or the WinList list-mode analysis package (Verity Software House, Topsham, Me.). The results are shown as single color histograms of Zot-FITC fluorescence intensity in T (CD3$^+$) and B (CD19$^+$) lymphocyte-gated populations.

B. Results

Figure 8:
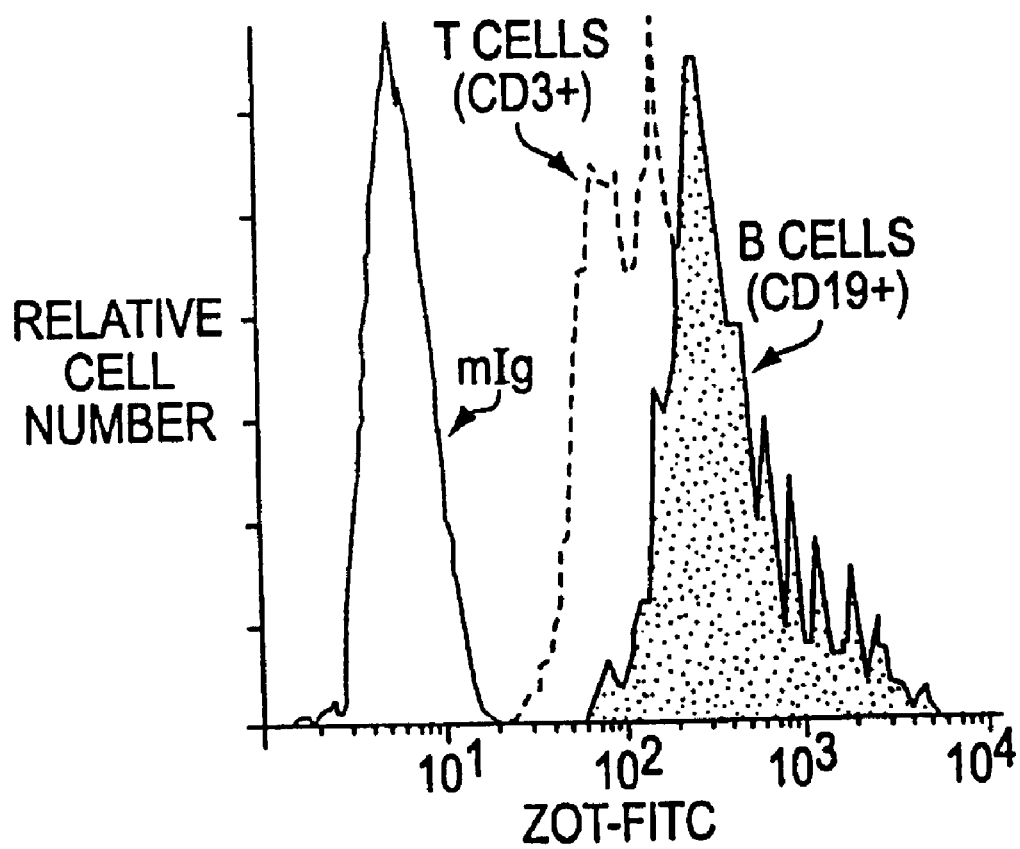
FIG. 8 illustrates the binding of FITC-Zot to human T and B lymphocytes. PBMC were incubated with Zot-FITC and mAb to molecules present in T (CD3$^+$) and B (CD19$^+$) lymphocytes and analyzed by flow cytometry. An isotopic FITC-labeled control mAb (mIg) corresponding to cells gated on the forward vs. side scatter lymphocyte region is also shown as an indicator of non-specific binding. The results indicate that Zot binds to both T and B lymphocytes.

An experiment showing the binding of Zot-F ITC to human T (CD3$^+$) and B (CD19$^+$) lymphocytes is shown in FIG. 8. The results indicate that Zot binds similarly to both, T and B lymphocytes. In this experiment Zot-FITC binding to macrophages was 5–8 fold higher than binding to T or B lymphocytes.

EXAMPLE 7

Inability of Zot Antagonists to Block Zot-FITC Binding

A. Material and Methods

Isolation of Human Peripheral Blood Mononuclear Cells (PBMC) From Healthy Volunteers PBMC were isolated from healthy volunteers as described above in Example 4.

Preparation of Purified 6xHis-Zot

The preparation of 6xHis-Zot was as described in Example 2 above.

Preparation of FZI/0 and FZI/1 Zot Antagonists

Peptide antagonists FZI/0 (Gly Gly Val Leu Val Gln Pro Gly) (SEQ ID NO:7) and FZI/1 (Val Gly Val Leu Gly Arg Pro Gly) (SEQ ID NO:8) were chemically synthesized and purified using well-known techniques, such as described in *High Performance Liquid Chromatography of Peptides and Proteins: Separation Analysis and Conformation*, Eds. Mant et al, C.R.C. Press (1991), and a peptide synthesizer, such as Symphony (Protein Technologies, Inc).

Conjugation of Zot to Fluorescein Isothiocyanate (Zot-FITC)

Conjugation of Zot with FITC was as performed in Example 6 above.

Culture Conditions for Blocking of FITC-Zot Binding to Human PBMC and Flow Cytometric Analysis PBMC isolated as described above were stained with mAbs to CD14 conjugated to PE and to CD3 conjugated to ECD (energy coupled dye, a PE-Texas-Red conjugate). Cells were then washed and incubated for 15 min at 4° C. in 400 μl of AIM-V medium (GIBCO BRL, a defined serum-free medium used routinely for human lymphocyte cultures) with 0.2% (w/v) NaAzide (to block internalization/recycling) in media alone or with the addition of FZI/0 (4.0 mg/ml), FZI/1 (4.0 mg/ml), BSA (4.0 mg/ml; negative control) or unlabeled Zot (160 μg/ml; positive control). Zot-FITC was then added to each tube to reach a final concentration of 40 μg/ml and incubated for 5 min (the time required to reach equilibrium), washed and immediately run in the flow cytometer. Thus, FZI/0, FZI/1 and BSA were added at 100-fold excess and unlabeled Zot at 4-fold excess compared to the concentration of Zot-FITC added. Unfortunately, the technical difficulties in obtaining large amounts of purified unlabeled Zot preparations precluded evaluating its ability to block Zot-FITC binding at more than 4-fold excess. Platelets, erythrocytes (if any) and cell debris were excluded from analysis by setting an appropriate gate on the forward vs. 90% light scatter parameters. For each sample we collected data for over 10,000 cells. Data analysis was performed using the Epics Elite analysis package (Coulter) or the WinList list-mode analysis package (Verity Software House, Topsham, Me.). The results are shown as % suppression of the mean fluorescence intensity of cells incubated with Zot-FITC in the presence of Zot antagonists, unlabeled Zot or BSA as related to the mean fluorescence intensity of cells incubated in media alone (arbitrarily assigned a value of 100%).

B. Results

Figure 9:
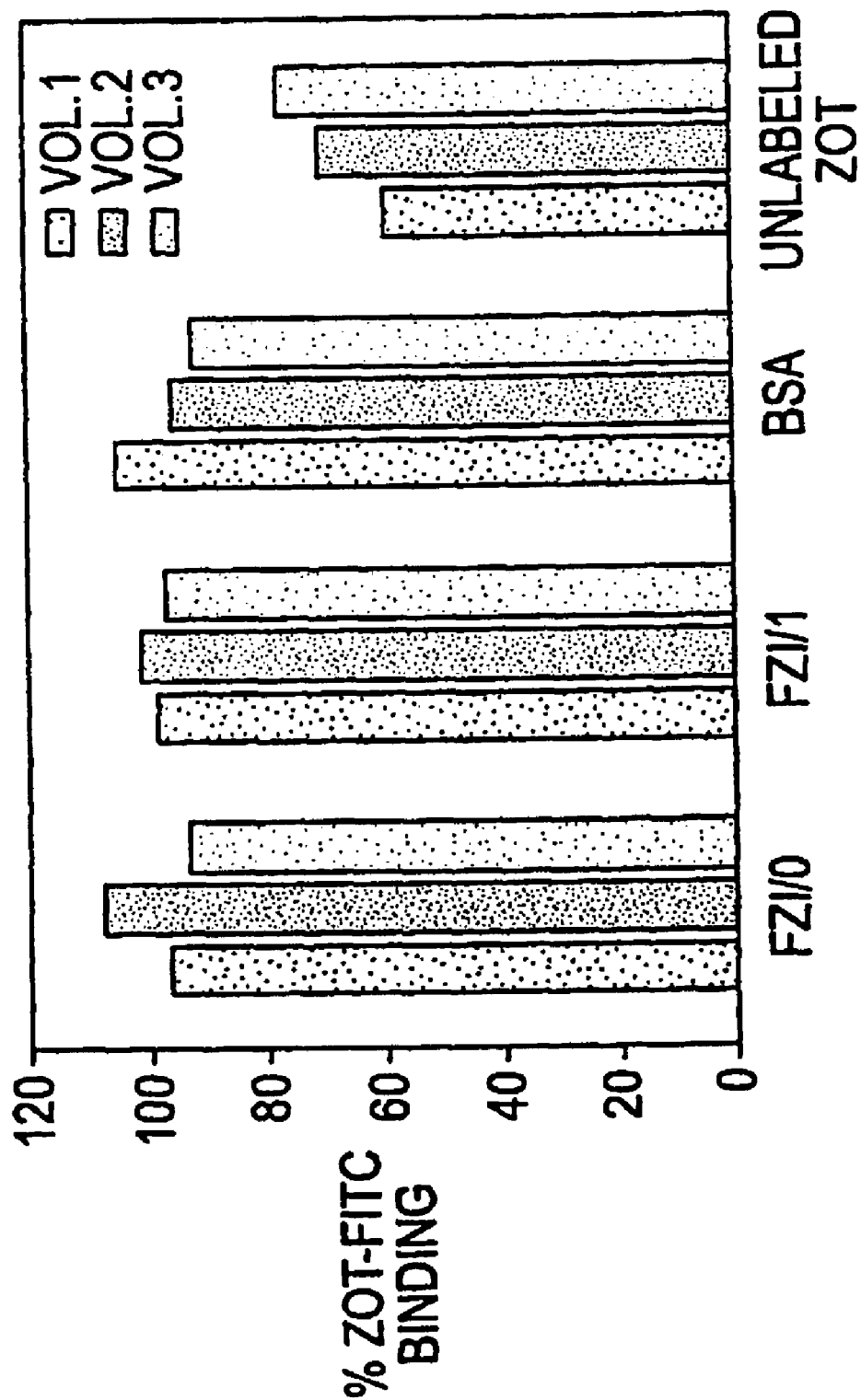
FIG. 9 illustrates the inability of Zot antagonists to block Zot-FITC binding. PBMC stained with CD14-PE and CD3-ECD were washed and incubated for 15 min at 4° C. in AIM-V medium alone or with the addition of 100-fold excess of FZI/0 (SEQ ID NO:7), FZI/1 (SEQ ID NO:8), BSA (negative control) or 4-fold excess of unlabeled Zot (positive control). Cells were then incubated with Zot-FITC and analyzed by flow cytometry. The results are expressed as % suppression of the mean fluorescence intensity of cells incubated with Zot-FITC in the presence of Zot antagonists, unlabeled Zot or BSA as related to the mean fluorescence intensity of cells incubated in media alone (arbitrarily assigned a value of 100%). The results show that the addition of either FZI/0 or FZI/1 Zot antagonists did not significantly block binding of Zot-FITC to CD14$^+$ gated macrophages. In contrast, pre-incubation with unlabeled Zot blocked binding of Zot-FITC by 24–43%.

A representative experiment showing the effects of incubation of PBMC from 3 different volunteers with Zot antagonists, unlabeled Zot or BSA is shown in FIG. 9. The addition of either FZI/0 or FZI/1 Zot antagonists at 100-fold excess did not significantly block binding of Zot-FITC to CD14+ gated macrophages. Similarly, addition of 100 fold excess BSA did not affect binding of Zot-FITC. In contrast, pre-incubation with only 4-fold excess unlabeled Zot blocked binding of Zot-FITC by 24–43%. These results suggest that binding of Zot to human macrophages involves a receptor with different binding sites that those of Zot/zonulin receptors identified in brain and intestinal tissues.

EXAMPLE 8

Zot Suppression of Tetanus Toxoid (TT)-Induced Proliferation is Dependent on Factor(s) Present in Serum A. Material and Methods Isolation of Human Peripheral Blood Mononuclear Cells (PBMC) From Healthy Volunteers PBMC were isolated from healthy volunteers as described in Example 4 above.

Preparation of Purified 6×His-Zot

The preparation of 6×His-Zot was as described in Example 2 above.

Culture Conditions and Lymphoproliferation Assays

PBMC ($1.5\times10^6$ cells/ml) were cultured in 1.0 ml of either (a) AIM-V medium, (b) RPMI 1640 containing 10% (v/v) heat-inactivated fetal calf serum and 50 µg/ml gentamicin or (c) RPMI 1640 containing 10% (v/v) heat-inactivated human AB serum and 50 µg/ml gentamicin. Cells were incubated at 37° C., 5% $CO_2$ in 96-well plates in the absence or presence of tetanus toxoid (TT; a specific antigen, used at 2.0 µg/ml; Wyeth, Marietta, PA) without or with purified Zot (60 µg/ml) or bovine serum albumin (BSA; a control protein, 60 µg/ml; Fraction V, Sigma, St. Louis, Mo.). Cells were cultured for 6 days and 1.0 Ci/well of tritiated thymidine was added. Plates were harvested 20 hr later on a Wallac cell harvester (Gaithersburg, Md.) and incorporated thymidine measured on a Wallac Trilux Microbeta counter (Gaithersburg, Md.).

B. Results

The results from 3 independent experiments showed that no inhibition of TT-induced proliferation could be observed when PBMC were incubated in the absence of serum, e.g., when the AIM-V defined media was used in the cultures. In fact the reverse was observed in most cases, i.e., incubation with Zot in the absence of serum lead to increased proliferative responses to TT. In contrast, incubation with Zot resulted in marked suppression of TT-induced proliferation when cultures were performed in the presence of either FCS or human AB serum. In fact, the presence of human AB serum appears to mediate higher levels (up to 90%) of suppression of TT-induced proliferation than that observed in the presence of FCS.

EXAMPLE 9

Zot Suppression of CD14 Expression on Human Monocytes/Macrophages

A. Material and Methods

Isolation of Human Peripheral Blood Mononuclear Cells (PBMC) From Healthy Volunteers PBMC were isolated from healthy volunteers as described in Example 4 above.

Preparation of Purified 6×His-Zot

The preparation of 6×His-Zot was as described in Example 2 above.

Culture Conditions and Flow Cytometric Analysis

PBMC isolated as described above were incubated at 37° C., 5% $CO_2$ in 24-well plates for various time periods (4 hr to 7 days) in the absence or presence of tetanus toxoid (TT; a specific antigen, used at 2.0 µg/ml; Wyeth, Marietta, Pa.) without or with purified Zot (60 µg/ml) or bovine serum albumin (BSA; a control protein, 60 µg/ml; Fraction V, Sigma, St. Louis, Mo.). Cells were then stained with a mAb to CD14 conjugated to FITC and analyzed by flow cytometry. Platelets, erythrocytes (if any) and cell debris were excluded from analysis by setting an appropriate gate on the forward vs. 90% light scatter parameters. For each sample, data for over 10,000 cells was collected. Data analysis was performed using the Epics Elite analysis package (Coulter) or the WinList list-mode analysis package (verity Software House, Topsham, Me.). The results are shown as single color histograms of CD14 fluorescence on cells gated on the "monocyte region", defined based on the forward scatter vs. side scatter characteristics of human macrophages.

B. Results

Figure 10A:
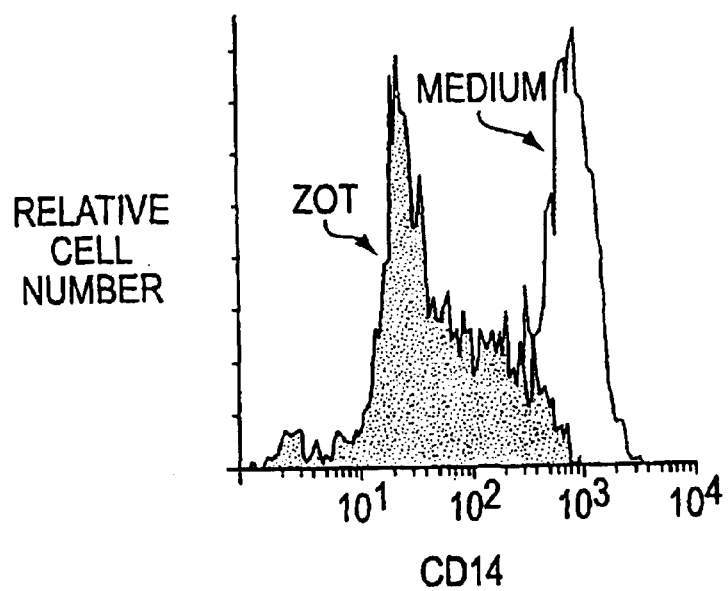
FIGS. 10A–10B illustrate Zot suppression of CD14 expression on human monocytes/macrophages. PBMC were incubated for 18 hr in the absence or presence of TT without or with purified Zot or BSA, stained with CD14-FITC and analyzed by flow cytometry. The results are shown as single color histograms of CD14 fluorescence on cells gated on the "monocyte region", defined based on the forward scatter vs. side scatter characteristics of human macrophages. The addition of Zot caused a marked suppression of the expression of CD14 in the absence of TT (FIG. 10A) or presence of TT (FIG. 10B).
Figure 10B:
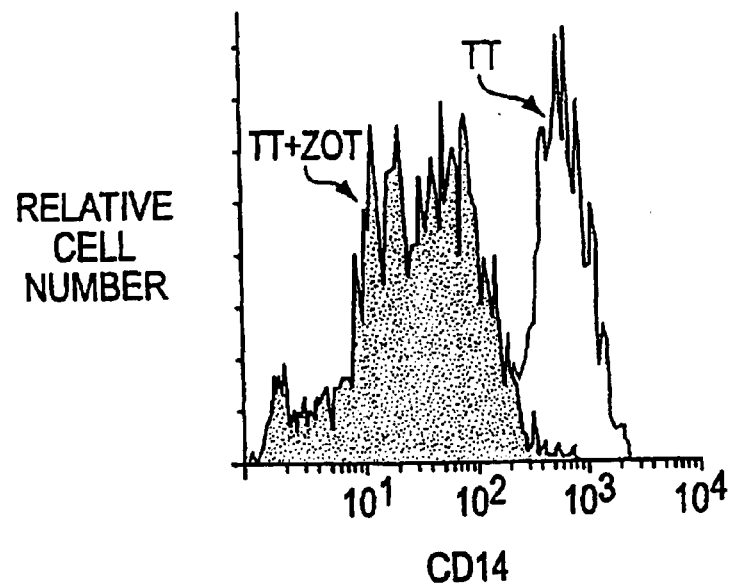

A representative experiment showing the effects of incubation of PBMC with Zot on the expression of CD14 in human macrophages is included in FIGS. 10A–10B. The addition of Zot caused a marked suppression of the expression of CD14 following 18 hr of incubation. This effect was very pronounced either in the absence (FIG. 10A) or presence (FIG. 10B) of tetanus toxoid. Addition of BSA did not affect CD14 expression. Kinetic experiments showed that Zot-induced suppression of CD14 expression is observed in approximately half of the experiments as early as 4–6 hr following exposure to Zot and that CD14 expression remains markedly suppressed after 7 days in culture (the last time point evaluated). CD14 is a molecule in the surface of macrophages that acts as a high-affinity receptor for LPS-LPS-binding protein complexes. Thus, down-regulation of CD14 expression by Zot is believed to have profound effects on macrophage activation and its ability to effectively initiate T cell-mediated immune responses.

EXAMPLE 10

Effects of Zot on the Viability of Human Lymphocytes and Monocytes/Macrophages

A. Material and Methods

Isolation of Human Peripheral Blood Mononuclear Cells (PBMC) from Healthy Volunteers PBMC were isolated from healthy volunteers as described in Example 4 above.

Preparation of Purified 6×His-Zot

The preparation of 6×His-Zot was as described in Example 2 above.

Culture Conditions and Flow Cytometric Analysis

PBMC isolated as described above were incubated at 37° C., 5% $CO_2$ in 24-well plates for various time periods (6 hr to 7 days) in the absence or presence of tetanus toxoid (TT; a specific antigen, used at 2.0 µg/ml; Wyeth, Marietta, Pa.) without or with purified Zot (40 µg/ml) or bovine serum albumin (BSA; a control protein, 40 µg/ml; Fraction V, Sigma, St. Louis, Mo.). Cells were then stained with dialyzed mAbs to CD14 conjugated to FITC and washed. To assess cell viability, propidium iodide (PI; 50 g/ml; a dye that is readily incorporated into dead cells but excluded from viable cells) was added to the cell suspensions and the samples analyzed immediately by flow cytometry. Platelets, erythrocytes (if any) and cell debris were excluded from analysis by setting an appropriate gate on the forward vs. 90% light scatter parameters. For each sample, data for over 10,000 cells was collected. Data analysis was performed using the Epics Elite analysis package (Coulter) or the WinList list-mode analysis package (Verity Software House, Topsham, Me.). The results are shown as the % viable cells gated on the "monocyte region" or "lymphocyte region", defined based on the forward scatter vs. side scatter characteristics of these cell populations.

B. Results

Figure 11:
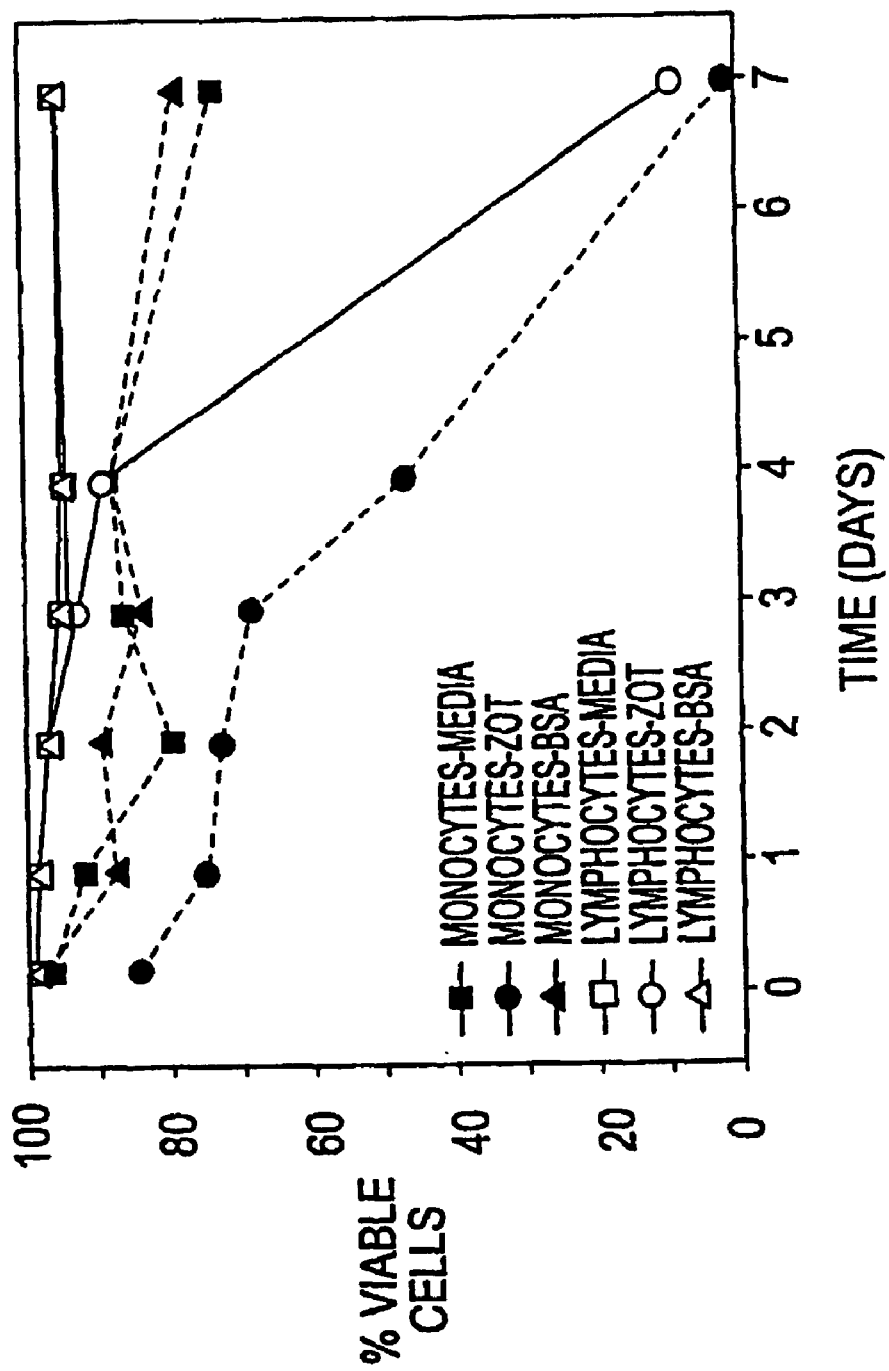
FIG. 11 illustrates the effects of Zot on human monocytes/macrophages and lymphocyte viability. PBMC were incubated for various time periods in the absence or presence of purified Zot or BSA. Cell viability was assessed using the propidium iodide exclusion test and flow cytometry. The results are shown as the % viable cells gated on the "monocyte region" or lymphocyte region", defined based on the forward scatter vs. side scatter characteristics of these cell populations. The results show that the addition of Zot affect macrophage viability at relatively early times, while the effects on lymphocytes did not become apparent until at least 4 days in culture.

A representative experiment showing the effects of incubation of PBMC with Zot on the viability of human macrophages and lymphocytes is included in FIG. 11. Addition of Zot caused moderate decreases in the viability of macrophages as compared to controls as early as 1 day in culture. These decreases became quite pronounced by day 4 and virtually all macrophages were dead after 7 days in culture. In contrast, no differences in lymphocyte viability were observed among cultures incubated with Zot and those incubated with media or BSA until day 4. However, lymphocyte viability was markedly decreased at later times in the presence of Zot. Similar results were observed when TT was added to the cultures in the absence or presence of Zot. These results demonstrate that Zot affect macrophage viability at relatively early times, while the effects on lymphocytes do not become apparent until at least 4 days in culture. These observations provide additional information concerning the mechanisms that may underlie Zot-mediated suppression of antigen processing and presentation, pointing to an early effect on macrophages.

EXAMPLE 11

Zot-mediated Induction of Cytokine Production by Human Monocytes/Macrophages and Lymphocytes A. Material and Methods Isolation of Human Peripheral Blood Mononuclear Cells (PBMC) From Healthy Volunteers PBMC were isolated from healthy volunteers as described in Example 4 above.

Preparation of Purified 6×His-Zot

The preparation of 6×His-Zot was as described in Example 2 above.

Culture Conditions

PBMC isolated as described above were incubated at 37° C., 5% $CO_2$ in 24-well plates for various time periods (6 hr to 4 days) in the absence or presence of tetanus toxoid (TT; a specific antigen, used at 2.0 µg/ml; Wyeth, Marietta, Pa.) without or with purified Zot (60 µg/ml) or bovine serum albumin (BSA; a control protein, 60 µg/ml; Fraction V, Sigma, St. Louis, Mo.). For studies involving the production of TNF-α, IL-11β and IL-10, the content of the wells were collected at 6 hr and at days 1, 2 and 4 into 1.5 ml Eppendorf tubes and centrifuged at 4° C. for 10 min at 2,700×g in a refrigerated Eppendorf centrifuge to remove cells and debris. Supernatants were then transferred to new Eppendorf tubes and frozen at −70° C. until analyzed. Supernatants for the measurement of T lymphocyte-derived cytokines (e.g., IL-2, IL-4 and IFN-γ) following stimulation with TT without or with purified Zot or BSA were collected after 3 days.

Cytokine Measurements by Chemiluminescence ELISA

A standard chemiluminescence capture ELISA was used to detect the presence of cytokines in the cell culture supernatants. Briefly, 1.0–2.0 µg/ml of anti-human cytokine antibodies were coated onto 96-well black opaque ELISA plates (Corning-Costar, lin Cambridge, Mass.) in either PBS (pH 7.4) (Biofluids) or 0.1 M sodium bicarbonate (pH 8.1) overnight at 4° C. Plates were washed with PBS (pH 7.4) containing 0.5% (v/v) Tween-20 (Sigma) and blocked for 2 hr with either PBS (pH 7.4) containing 10% (v/v) FCS or 4.0% (w/v) BSA. After washing, 100 µl of cell culture supernatants or recombinant human cytokines (as standards) were added to the wells and incubated for 2 hr at room temperature. After washing, the corresponding anti-cytokine mAbs conjugated to biotin were added to the wells (45 min at room temperature), washed and incubated with avidin-peroxidase for 30 min at room temperature. BM chemiluminescence ELISA reagent (Boehringer Mannheim, Gaithersburg, Md.) was then added and chemiluminescence detected on a 1450 Microbeta Trilux plate reader (Wallac, Gaithersburg, Md.). The anti-IL-1β antibodies were obtained from Endogen (Woburn, Mass.), all others were obtained from Pharmingen (San Diego, Calif.).

B. Results

Figure 12A:
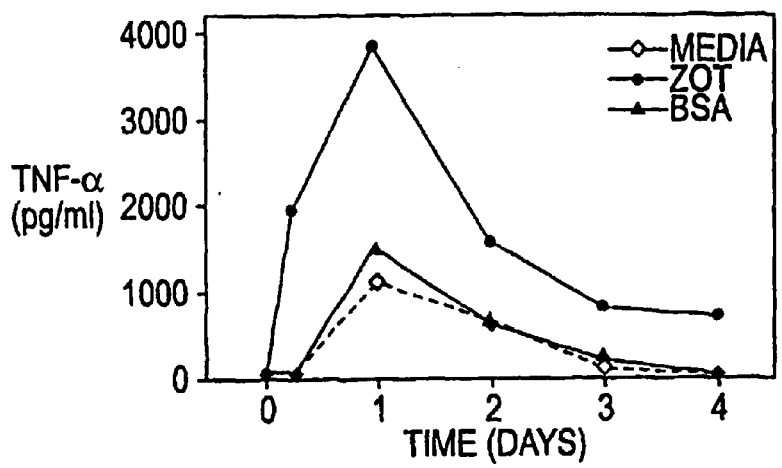
FIGS. 12A–12C illustrates Zot-mediated induction of cytokine production by human monocytes/macrophages. PBMC were incubated for 6 hr to 4 days in the absence or presence of purified Zot or BSA. Supernatants were collected at the indicated times and cytokine levels measured by chemiluminescence ELISA. Addition of Zot resulted in in the production of high levels of TNF-α(FIG. 12A) and IL-10 (FIG. 12C) as early as 6 hr, reaching peak levels at 24 hr. A weak induction of IL-1β production was also observed (FIG. 12B).
Figure 12B:
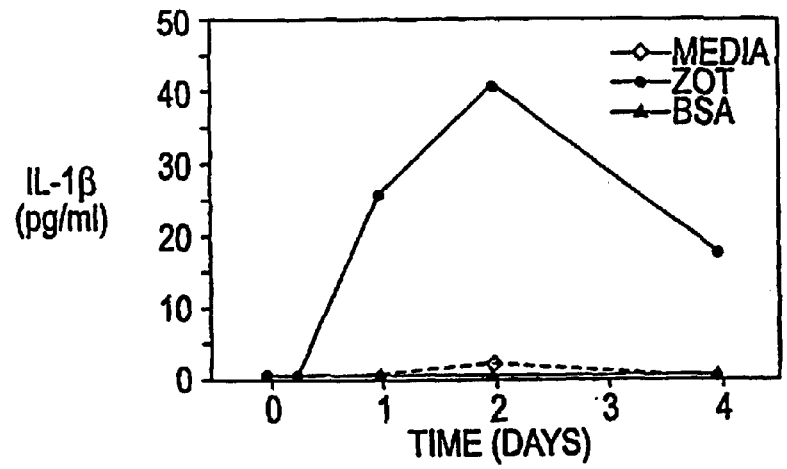
Figure 12C:
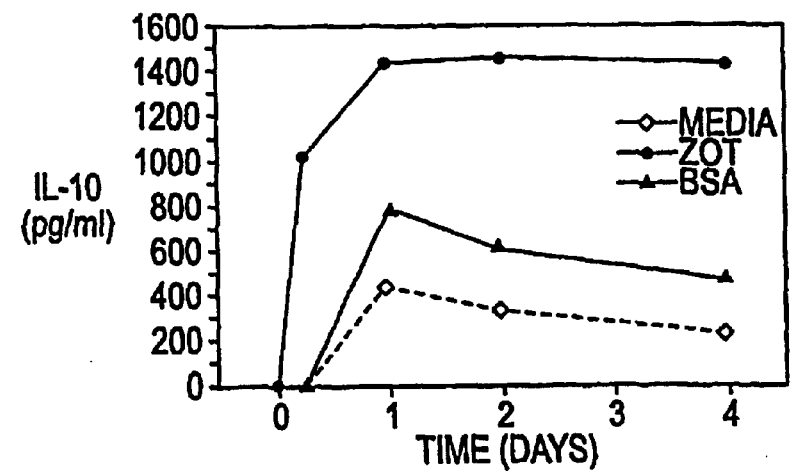

A representative experiment showing the ability of Zot to induce cytokine production by human macrophages is shown in FIGS. 12A–12C. Addition of Zot (in the absence of TT) induced the production of considerable amounts of TNF-α as early as 6 hr, reaching peak levels at 24 hr (3,400–3,800 pg/ml) and decreasing afterwards reaching near-baseline levels by 4 days (FIG. 12A). Lower levels of TNF-α were observed in media or BSA cultures (~1,000–1, 100 pg/ml), probably the result of non-specific activation of macrophages following adherence to plastic. A weak induction of IL-1β by Zot (~40–60 pg/ml) was also observed that reached peak levels after 2 days and decreased considerably by day 4 (~20 pg/ml) (FIG. 12B). No significant levels of IL-1β were observed in media or BSA cultures. Finally, incubation with Zot resulted in the production of high levels of IL-10 after 6 hr (~1,000 pg/ml), reaching peak levels by day 1 (~1,500 pg/ml) and remaining at the same concentrations up to day 4 (FIG. 12C). Similar to the findings described above for TNF-α, considerably lower levels of IL-10 were observed in media or BSA cultures, probably the result of non-specific activation of macrophages following adherence to plastic. The presence of TT did not alter either the kinetics or the magnitude of the cytokine responses observed following the addition of Zot. The induction of high levels of potent proinflammatory cytokines following exposure to Zot provides additional information concerning the mechanisms that may underlie Zot-mediated suppression of antigen processing and presentation, again pointing to an early effect on macrophages. For example, Zot-mediated induction of IL-10 production, a cytokine known to be a major inhibitor of the Th1 type response through the inhibition of the production of cytokines such as IL-2, is believed to play a significant role in the suppression of antigen-induced lymphoproliferative responses observed when Zot is added to the cultures.

Figure 13A:
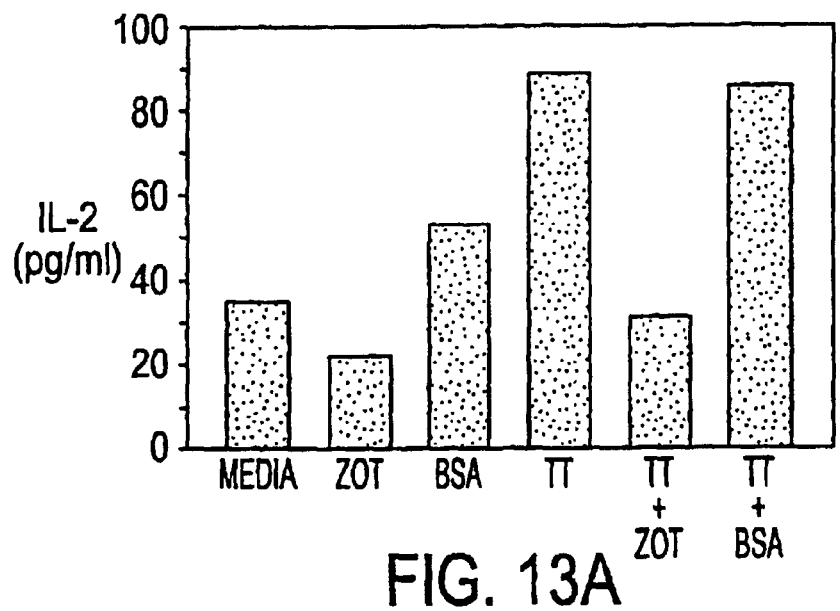
FIGS. 13A–13B illustrate Zot-mediated induction of cytokine production by human lymphocytes. PBMC were incubated for 3 days without or with TT in the absence or presence of purified Zot or BSA and cytokine levels in the supernatants measured by chemiluminescence ELISA. Addition of Zot resulted in the suppression of IL-2 production induced by incubation with TT, while no measurable levels of IL-2 were induced by Zot in the absence of TT (FIG. 13A). In contrast, addition of Zot consistently induced the production of IFN-γ in the absence of TT, similar to the levels induced by TT, and markedly increased the levels of IFN-γ induced by TT (FIG. 13B).
Figure 13B:
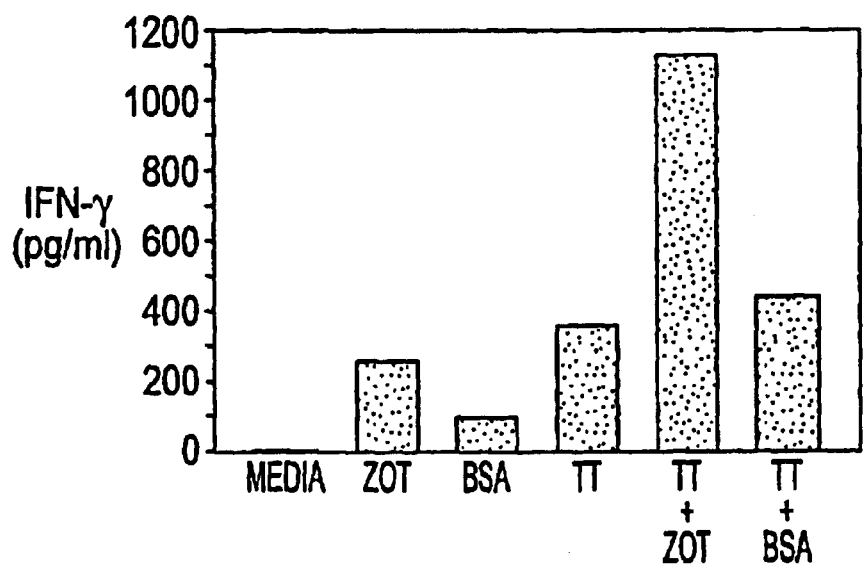

A representative experiment showing the effects of Zot on the production of T cell-derived cytokines is shown in FIGS. 13A–13B. It was observed that the addition of Zot suppressed IL-2 production induced by incubation with TT, while BSA had no effect (FIG. 13A). No measurable levels of IL-2 were induced by Zot in the absence of TT. In contrast, addition of Zot consistently induced the production of low to moderate levels of IFN-γ in the absence of TT, similar to the levels induced by TT (FIG. 13B). Moreover, Zot markedly increased the levels of IFN-induced by TT, while BSA had no effect (FIG. 13B). Finally, it as observed that the addition of Zot did not induce IL-4 production. Since IL-2 is a cytokine that plays a critical role in lymphocyte proliferation, suppression of the production of IL-2 following antigenic stimulation is believed to be one of the key mechanisms underlying Zot-mediated suppression of TT induced proliferation. Also of importance, the fact that Zot induces IFN-γ production in the absence or presence of TT, as well as the production of many pro-inflammatory cytokines, indicates that Zot exerts its immunoregulatory effects at various levels during the complex process of antigen processing and presentation leading to the generation of antigen-specific immune responses.

All references cited herein are incorporated by reference in their entirety.

While the invention has been described in detail, and with reference to specific embodiments thereof, it will be apparent to one with ordinary skill in the art that various changes and modifications can be made therein without departing from the spirit and scope thereof.

What is claimed is:

1. A method of suppressing antigen presenting cell-mediated lymphocyte proliferation in a culture of cells pre-exposed to a particular antigen comprising the step of contacting the culture with an amount of Zot, said amount effective to down regulate the activity of said antigen presenting cell.

2. A method of suppressing antigen presenting cell-mediated lymphocyte proliferation in a culture of cells in response to an antigen comprising the step of contacting the culture with an amount effective to down regulate the activity of said antigen presenting cell of Zot in combination with said antigen, said amount effective to down regulate the activity of said antigen presenting cell.

* * * * *